(12) United States Patent
Suarez et al.

(10) Patent No.: US 8,753,346 B2
(45) Date of Patent: Jun. 17, 2014

(54) TOOL, KIT-OF-PARTS FOR MULTI-FUNCTIONAL TOOL, AND ROBOTIC SYSTEM FOR SAME

(75) Inventors: Joseph Suarez, Plantation, FL (US); Brian D. Schmitz, Fort Lauderdale, FL (US); Hyosig Kang, Weston, FL (US); Peter L. Ebbitt, Boca Raton, FL (US)

(73) Assignee: Mako Surgical Corp., Ft. Lauderdale, FL (US)

( * ) Notice: Subject to any disclaimer, the term of this patent is extended or adjusted under 35 U.S.C. 154(b) by 518 days.

(21) Appl. No.: 12/894,076

(22) Filed: Sep. 29, 2010

(65) Prior Publication Data

US 2011/0082462 A1    Apr. 7, 2011

Related U.S. Application Data

(60) Provisional application No. 61/278,066, filed on Oct. 1, 2009, provisional application No. 61/339,460, filed on Mar. 4, 2010, provisional application No. 61/339,756, filed on Mar. 9, 2010, provisional application No. 61/401,209, filed on Aug. 9, 2010.

(51) Int. Cl.
*A61B 17/00*    (2006.01)
*A61B 17/58*    (2006.01)

(52) U.S. Cl.
USPC ............................................. 606/91; 606/81

(58) Field of Classification Search
USPC .................. 606/81, 91, 99; 403/109.1–109.8; 74/493
See application file for complete search history.

(56) References Cited

U.S. PATENT DOCUMENTS

| | | | |
|---|---|---|---|
| 2,744,419 A * | 5/1956 | Chayne | 74/493 |
| 4,123,074 A | 10/1978 | Wanner | |
| 4,495,834 A * | 1/1985 | Bauer et al. | 74/493 |
| 5,806,518 A | 9/1998 | Mittelstadt | |
| 6,228,089 B1 | 5/2001 | Wahrburg | |
| 6,322,567 B1 | 11/2001 | Mittelstadt | |
| 7,344,329 B2 * | 3/2008 | Hutchinson et al. | 403/109.1 |
| 8,016,830 B2 * | 9/2011 | Veldman et al. | 606/86 R |
| 2004/0073226 A1 * | 4/2004 | Cotting et al. | 606/91 |

(Continued)

FOREIGN PATENT DOCUMENTS

| | | |
|---|---|---|
| CA | 2484666 A1 | 4/2005 |
| KR | 10719347 B1 | 5/2007 |
| WO | WO 02/060653 A2 | 8/2002 |

OTHER PUBLICATIONS

International Search Report and Written Opinion dated Jun. 15, 2011 as received in PCT/US2010/050740, 9 pages.

(Continued)

*Primary Examiner* — Matthew Lawson
(74) *Attorney, Agent, or Firm* — Foley & Lardner LLP

(57) ABSTRACT

A tool includes a housing including a receiving portion configured to receive at least a portion of an operating member so as to permit rotation of the operating member relative to the housing while constraining movement of the operating member in a radial direction of the operating member. The tool also includes a coupling device disposed on the housing and configured to couple the operating member to the housing so as to permit rotation of the operating member relative to the housing. The coupling device includes a retaining member configured to engage the operating member to constrain movement of the operating member relative to the housing in a longitudinal direction of the operating member. The retaining member is configured to rotate relative to the housing.

15 Claims, 39 Drawing Sheets

(56) References Cited

U.S. PATENT DOCUMENTS

| | | | |
|---|---|---|---|
| 2004/0243134 | A1 | 12/2004 | Walker et al. |
| 2006/0142657 | A1 | 6/2006 | Quaid et al. |
| 2006/0217730 | A1* | 9/2006 | Termanini ............... 606/81 |
| 2007/0123891 | A1* | 5/2007 | Ries et al. ............... 606/80 |
| 2007/0260253 | A1 | 11/2007 | Johnson et al. |
| 2007/0270685 | A1 | 11/2007 | Kang et al. |
| 2008/0004633 | A1 | 1/2008 | Arata et al. |
| 2008/0255568 | A1* | 10/2008 | Tornier et al. ............... 606/91 |
| 2008/0264196 | A1* | 10/2008 | Schindler et al. ............... 74/493 |
| 2009/0216374 | A1 | 8/2009 | Low et al. |
| 2010/0106511 | A1 | 4/2010 | Shirakawa |
| 2010/0166496 | A1 | 7/2010 | Bennett |
| 2010/0286826 | A1 | 11/2010 | Tsusaka et al. |

OTHER PUBLICATIONS

International Search Report and Written Opinion dated Jun. 16, 2011 as received in PCT/US2010/050754, 11 pages.

U.S. Appl. No. 12/894,071, filed Sep. 29, 2010, Hagag et al.

U.S. Appl. No. 12/894,080, filed Sep. 29, 2010, Ziaei et al.

Cruces et al., Cooperative Robotic System to Support Surgical Interventions, Medical Robotics, Jan. 2008, pp. 481-490, I-Tech Education and Publishing, Vienna, Austria.

Ortmaier et al., A Hands-on-Robot for Accurate Placement of Pedicle Screws, Proceedings of the 2006 IEEE International Conference on Robotics and Automation, Orlando, Florida, May 2006, pp. 4179-4186.

World Wide Web, http://www.modicas.de/fileadmin/modicas/img/produkte/Flyer.pdf, modiCAS Flyer, printed on Apr. 28, 2011.

International Preliminary Report on Patentability cited in related International Patent Application No. PCT/US2010/050740, dated Apr. 12, 2012.

* cited by examiner

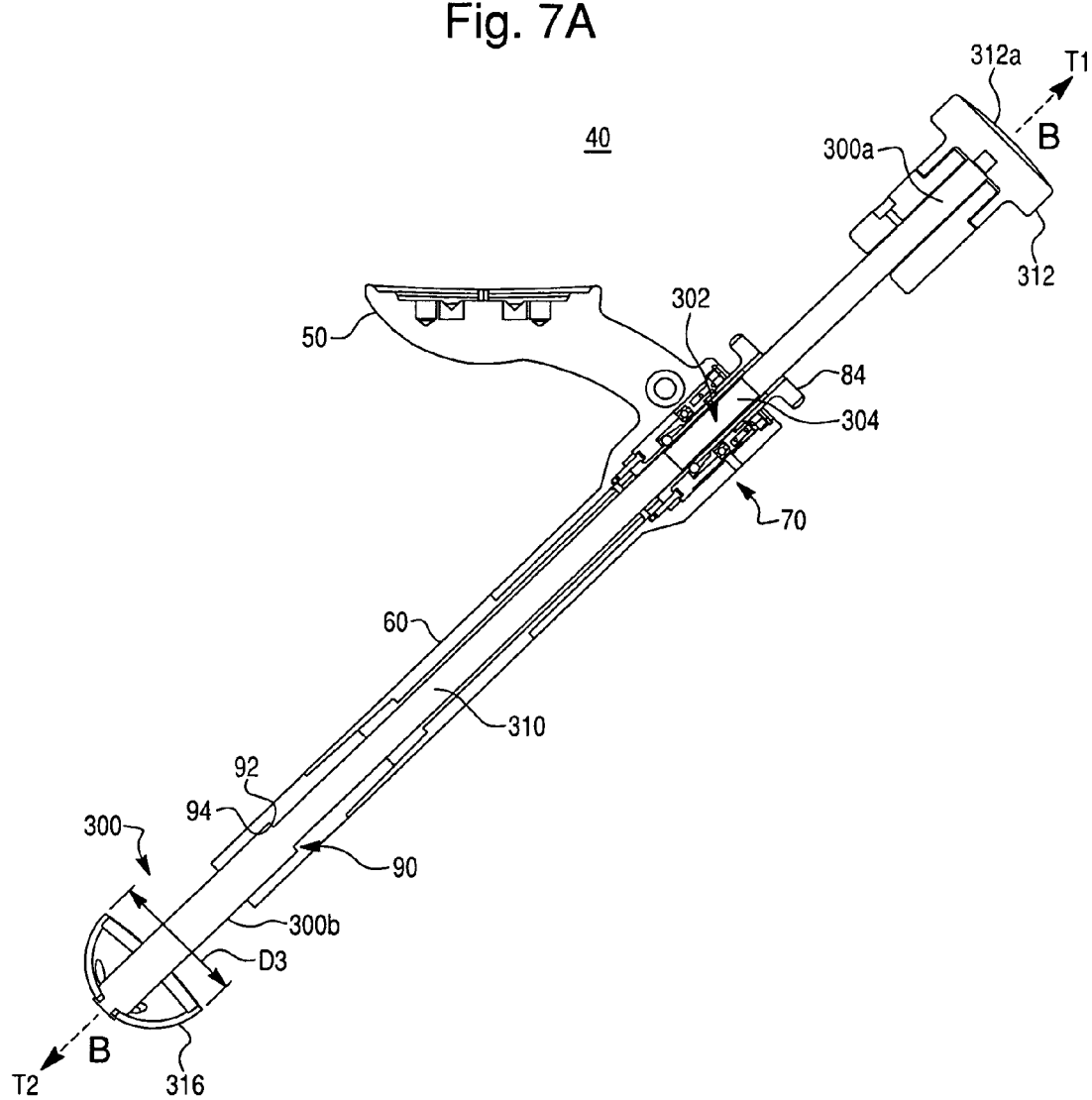

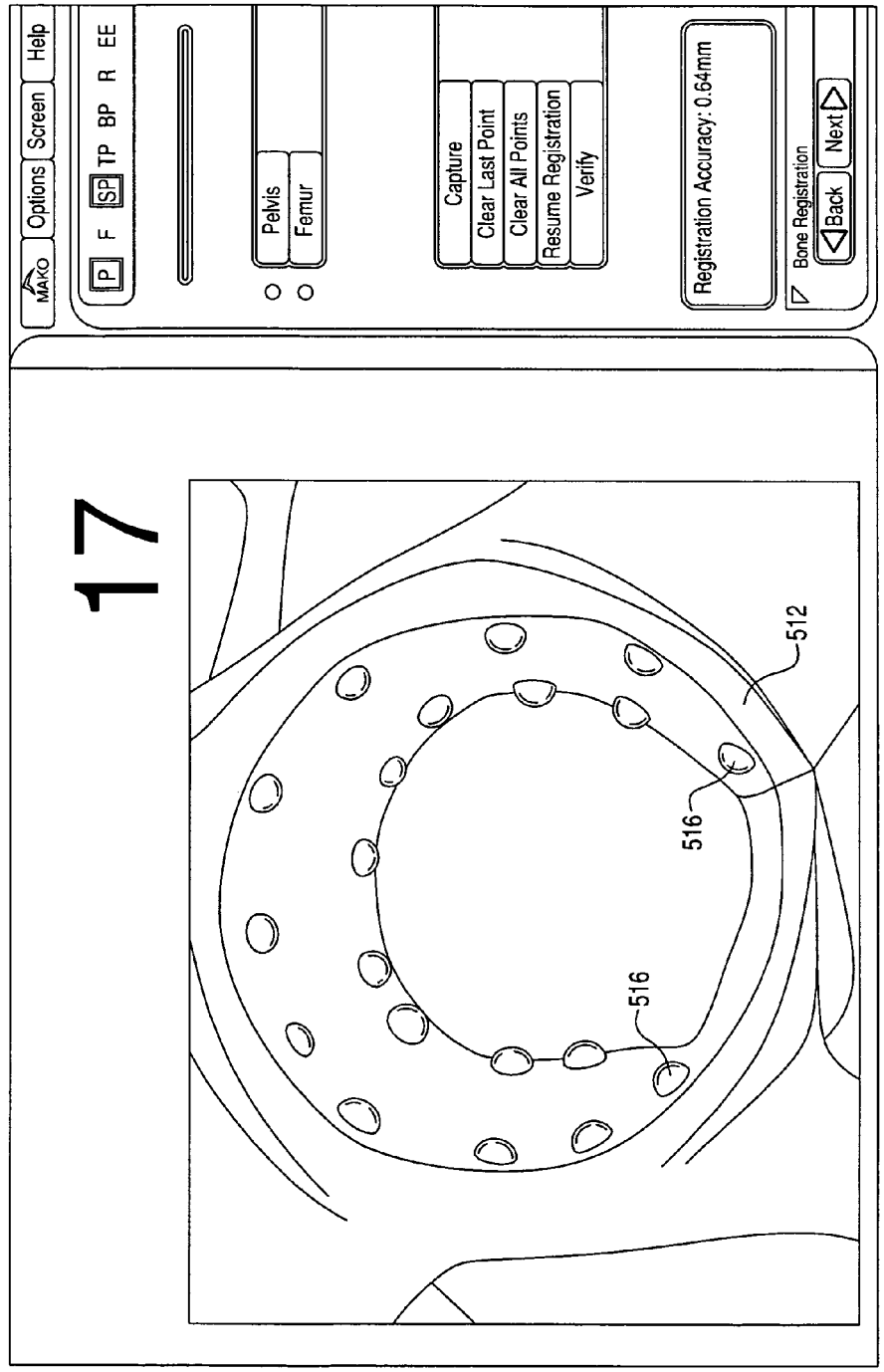

TOOL, KIT-OF-PARTS FOR MULTI-FUNCTIONAL TOOL, AND ROBOTIC SYSTEM FOR SAME

CROSS-REFERENCE TO RELATED PATENT APPLICATIONS

This application claims priority to U.S. Provisional Patent Application Ser. No. 61/278,066, filed Oct. 1, 2009; U.S. Provisional Patent Application Ser. No. 61/339,460, filed Mar. 4, 2010; U.S. Provisional Patent Application Ser. No. 61/339,756, filed Mar. 9, 2010; and U.S. Provisional Patent Application Ser. No. 61/401,209, filed Aug. 9, 2010, each of which is hereby incorporated by reference in its entirety.

BACKGROUND OF THE INVENTION

1. Field of Invention

The present invention relates generally to robotic systems and, more particularly, to tools for surgical systems for orthopedic joint replacement surgery.

2. Description of Related Art

Robotic systems are often used in applications that require a high degree of accuracy and/or precision, such as surgical procedures or other complex tasks. Such systems may include various types of robots, such as autonomous, teleoperated, and interactive.

Interactive robotic systems are preferred for some types of surgery, such as joint replacement surgery, because they enable a surgeon to maintain direct, hands-on control of the surgical procedure while still achieving a high degree of accuracy and/or precision. For example, in knee replacement surgery, a surgeon can use an interactive, haptically guided robotic arm in a passive manner to sculpt bone to receive a joint implant, such as a knee implant. To sculpt bone, the surgeon manually grasps and manipulates the robotic arm to move a cutting tool (such as a burr) that is coupled to the robotic arm to cut a pocket in the bone. As long as the surgeon maintains a tip of the burr within a predefined virtual cutting boundary defined, for example, by a haptic object, the robotic arm moves freely with low friction and low inertia such that the surgeon perceives the robotic arm as essentially weightless and can move the robotic arm as desired. If the surgeon attempts to move the tip of the burr to cut outside the virtual cutting boundary, however, the robotic arm provides haptic (or force) feedback that prevents or inhibits the surgeon from moving the tip of the burr beyond the virtual cutting boundary. In this manner, the robotic arm enables highly accurate, repeatable bone cuts. When the surgeon manually implants a knee implant (such as a patellofemoral component) on a corresponding bone cut the implant will generally be accurately aligned due to the configuration of and interface between the cut bone and the knee implant.

The above-described interactive robotic system, though useful for knee replacement surgery, is not optimally suited for types of surgery, such as hip replacement surgery, that require the use of multiple surgical tools having different functions (e.g., reaming, impacting), different configurations (e.g., straight, offset), and different weights. A system designed to accommodate a variety of tools may be prohibitively complex and require multiple end effectors, and removing and attaching different types of tools to the robotic arm during a surgical procedure could increase the time to perform the procedure. Additionally, in hip replacement surgery, in addition to maintaining an appropriate cutting boundary, angular orientation of surgical tools and implants is important. For example, in conventional hip replacement surgery, the surgeon uses a hemispherical reamer to resurface a patient's acetabulum, which is a cup-shaped socket in the pelvis. Then, a corresponding cup-shaped implant (an acetabular cup), is attached to a distal end of an impactor tool. The surgeon implants the acetabular cup into the reamed socket by repeatedly striking a proximal end of the impactor tool with a mallet. Angular orientation of both the reamed socket and the implanted acetabular cup is important because incorrect individual and/or relative orientation can result in misalignment of the acetabular cup to the appropriate version and inclination angles of the patient's acetabular anatomy. Misalignment can lead to post-operative problems, including joint dislocation, impingement of the femur on the acetabular cup at the extreme ranges of motion of the femur, and accelerated wear of the acetabular cup due to improper loading of the femoral head-to-acetabular cup interface. Alignment is also important to maintain correct leg length and medial/lateral offset. Finally, impacting the acetabular cup into the reamed socket generates high impact forces that could potentially damage a robotic arm designed for highly accurate and/or precise operation.

In view of the foregoing, a need exists for an improved robotic surgical system and components thereof.

SUMMARY

According to an aspect of the present invention, a tool includes a housing including a receiving portion configured to receive at least a portion of an operating member so as to permit rotation of the operating member relative to the housing while constraining movement of the operating member in a radial direction of the operating member. The tool also includes a coupling device disposed on the housing and configured to couple the operating member to the housing so as to permit rotation of the operating member relative to the housing. The coupling device includes a retaining member configured to engage the operating member to constrain movement of the operating member relative to the housing in a longitudinal direction of the operating member. The retaining member is configured to rotate relative to the housing.

According to another aspect, a kit-of-parts for a multi-functional tool includes a first operating member configured to have a first function and a second operating member configured to have a second function. The first operating member has a first coupling region, and the second operating member has a second coupling region. The kit-of-parts includes a housing including a receiving portion configured to individually and interchangeably receive at least a portion of the first operating member and the second operating member so as to permit rotation of the received operating member relative to the housing while constraining movement of the received operating member in a radial direction of the received operating member. A coupling device is disposed on the housing and is configured to couple the received operating member to the housing so as to permit rotation of the received operating member relative to the housing. The coupling device includes a retaining member configured to engage a corresponding one of the first coupling region and the second coupling region to constrain movement of the received operating member relative to the housing in a longitudinal direction of the received operating member. The coupling device and first and second operating members are configured so as to constrain the movement of the received operating member in the longitudinal direction to a first region of constraint when the coupling device engages the first coupling region of the first operating member and to a second region of constraint, which is different from the first region of constraint, when the coupling device engages the second coupling region of the second operating member According to yet another aspect, a robotic system includes a first operating member, a second operating member, a robotic arm, a housing coupled to the robotic arm, and a coupling device disposed on the housing. The first operating member comprises at least one of a straight reamer shaft and an offset reamer shaft, and the second operating member comprises at least one of a straight impactor shaft and an offset impactor shaft. The housing includes a receiving portion configured to individually and interchangeably receive at least a portion of the first operating member and the second operating member so as to permit rotation of the received operating member relative to the housing while constraining movement of the received operating member in a radial direction of the received operating member. The coupling device is disposed on the housing and is configured to couple the received operating member to the housing so as to permit rotation of the first operating member about a longitudinal axis of the first operating member and to permit movement of the second operating member along a longitudinal axis of the second operating member.

BRIEF DESCRIPTION OF THE DRAWINGS

The accompanying drawings, which are incorporated and constitute a part of this specification, illustrate embodiments of the invention and together with the description serve to explain aspects of the invention.

FIG. 7A is a cross-sectional view of the end effector of FIG. 4A coupled to another embodiment of an operating member in a seated position.

FIGS. 14A-14G illustrate embodiments of a computer display for use during a surgical procedure.

DETAILED DESCRIPTION OF PREFERRED EMBODIMENTS

Figure 1A:
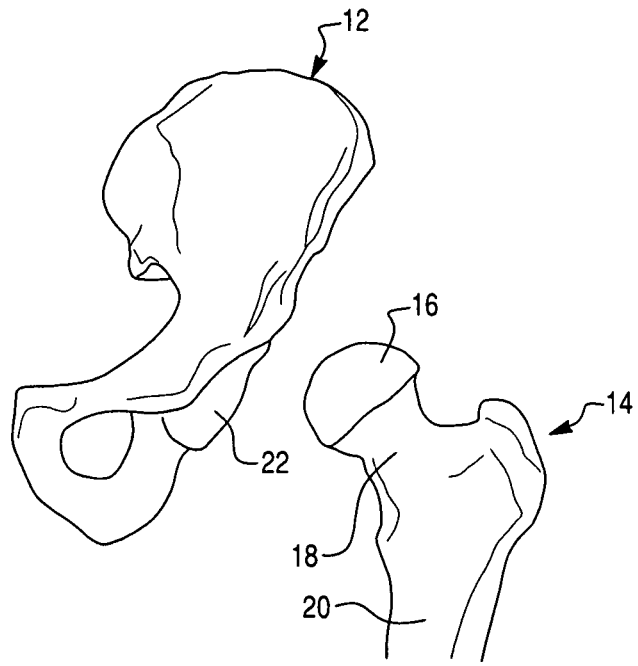
FIG. 1A is a perspective view of a femur and a pelvis.

Presently preferred embodiments of the invention are illustrated in the drawings. An effort has been made to use the same or like reference numbers throughout the drawings to refer to the same or like parts. Although this specification refers primarily to a robotic arm for orthopedic hip replacement, it should be understood that the subject matter described herein is applicable to other types of robotic systems, including those used for surgical and non-surgical applications, as well as to other joints of the body, such as, for example, a shoulder joint.

Overview

Figure 1B:
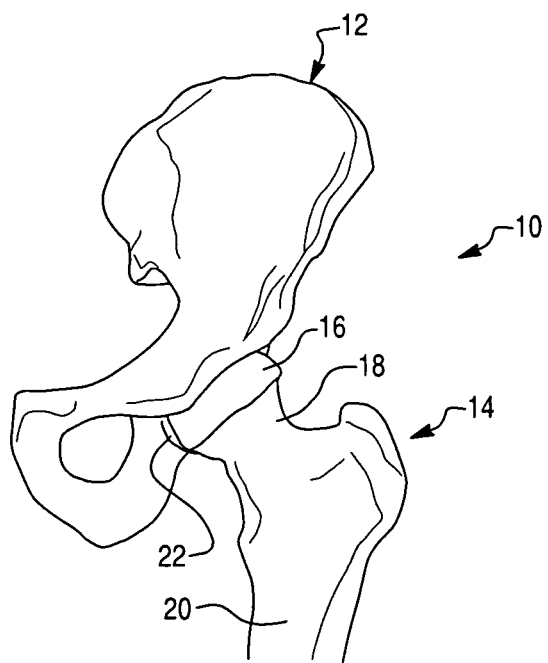
FIG. 1B is a perspective view of a hip joint formed by the femur and pelvis of FIG. 1A.

The hip joint is the joint between the femur and the pelvis and primarily functions to support the weight of the body in static (for example, standing) and dynamic (for example, walking) postures. FIG. 1A illustrates the bones of a hip joint 10, which include a pelvis 12 (shown in part) and a proximal end of a femur 14. The proximal end of the femur 14 includes a femoral head 16 disposed on a femoral neck 18. The femoral neck 18 connects the femoral head 16 to a femoral shaft 20. As shown in FIG. 1B, the femoral head 16 fits into a concave socket in the pelvis 12 called the acetabulum 22, thereby forming the hip joint 10. The acetabulum 22 and femoral head 16 are both covered by articular cartilage that absorbs shock and promotes articulation of the joint 10.

Figure 2A:
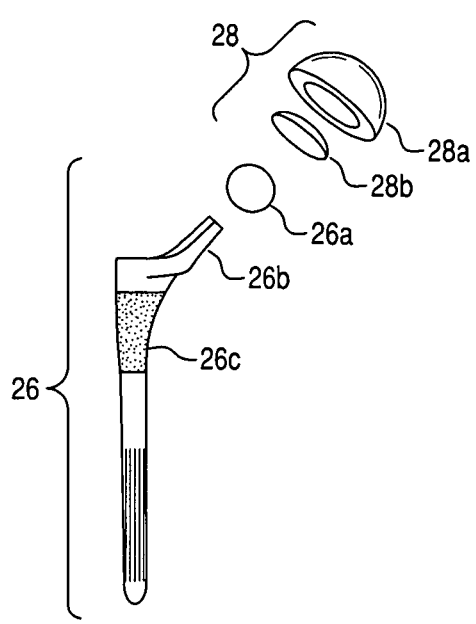
FIG. 2A is an exploded perspective view of a femoral component and an acetabular component for a total hip replacement procedure.
Figure 2B:
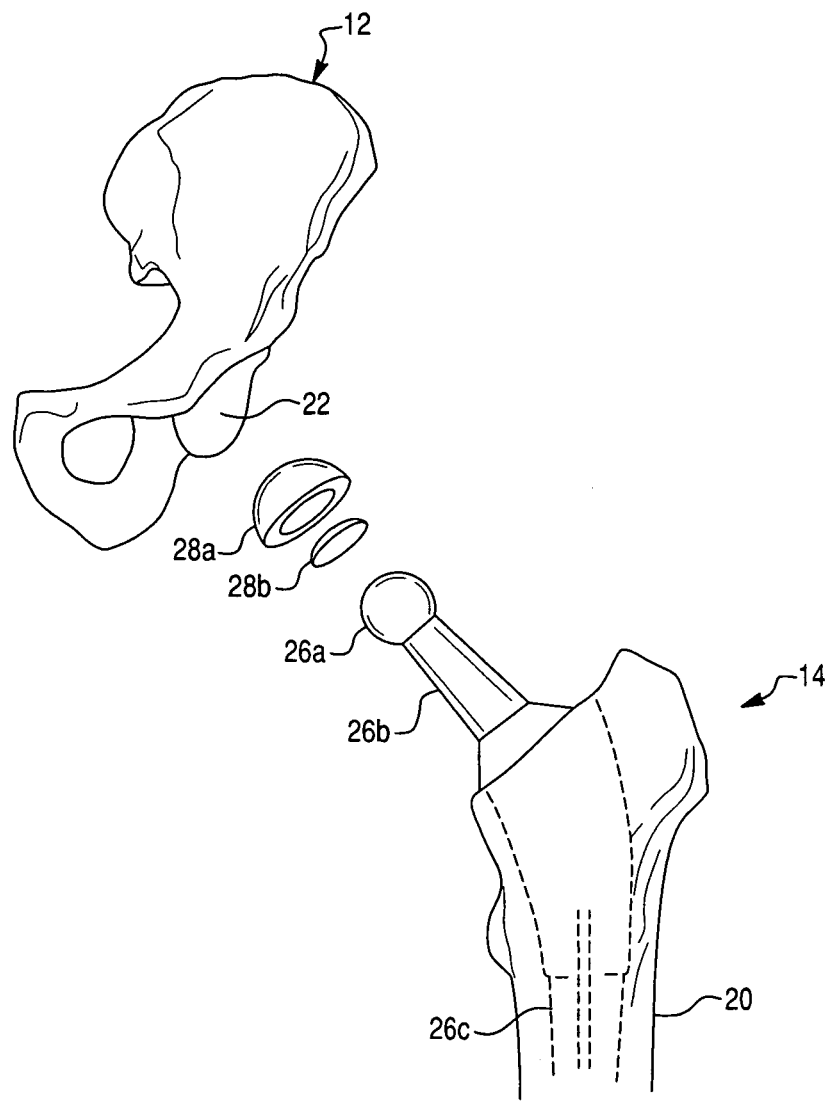
FIG. 2B is a perspective view illustrating placement of the femoral component and acetabular component of FIG. 2A in relation to the femur and pelvis of FIG. 1A, respectively.

Over time, the hip joint 10 may degenerate (for example, due to osteoarthritis) resulting in pain and diminished functionality. As a result, a hip replacement procedure, such as total hip arthroplasty or hip resurfacing, may be necessary. During hip replacement, a surgeon replaces portions of a patient's hip joint 10 with artificial components. In total hip arthroplasty, the surgeon removes the femoral head 16 and neck 18 and replaces the natural bone with a prosthetic femoral component 26 comprising a head 26a, a neck 26b, and a stem 26c (shown in FIG. 2A). As shown in FIG. 2B, the stem 26c of the femoral component 26 is anchored in a cavity the surgeon creates in the intramedullary canal of the femur 14. Alternatively, if disease is confined to the surface of the femoral head 16, the surgeon may opt for a less invasive approach in which the femoral head is resurfaced (e.g., using a cylindrical reamer) and then mated with a prosthetic femoral head cup (not shown). Similarly, if the natural acetabulum 22 of the pelvis 12 is worn or diseased, the surgeon resurfaces the acetabulum 22 using a reamer and replaces the natural surface with a prosthetic acetabular component 28 comprising a hemispherical shaped cup 28a (shown in FIG. 2A) that may include a liner 28b. To install the acetabular component 28, the surgeon connects the cup 28a to a distal end of an impactor tool and implants the cup 28a into the reamed acetabulum 22 by repeatedly striking a proximal end of the impactor tool with a mallet. If the acetabular component 28 includes a liner 28b, the surgeon snaps the liner 28b into the cup 28a after implanting the cup 28a. Depending on the position in which the surgeon places the patient for surgery, the surgeon may use a straight or offset reamer to ream the acetabulum 22 and a straight or offset impactor to implant the acetabular cup 28a. For example, a surgeon that uses a postero-lateral approach may prefer straight reaming and impaction whereas a surgeon that uses an antero-lateral approach may prefer offset reaming and impaction.

Exemplary Robotic System

Figure 3A:
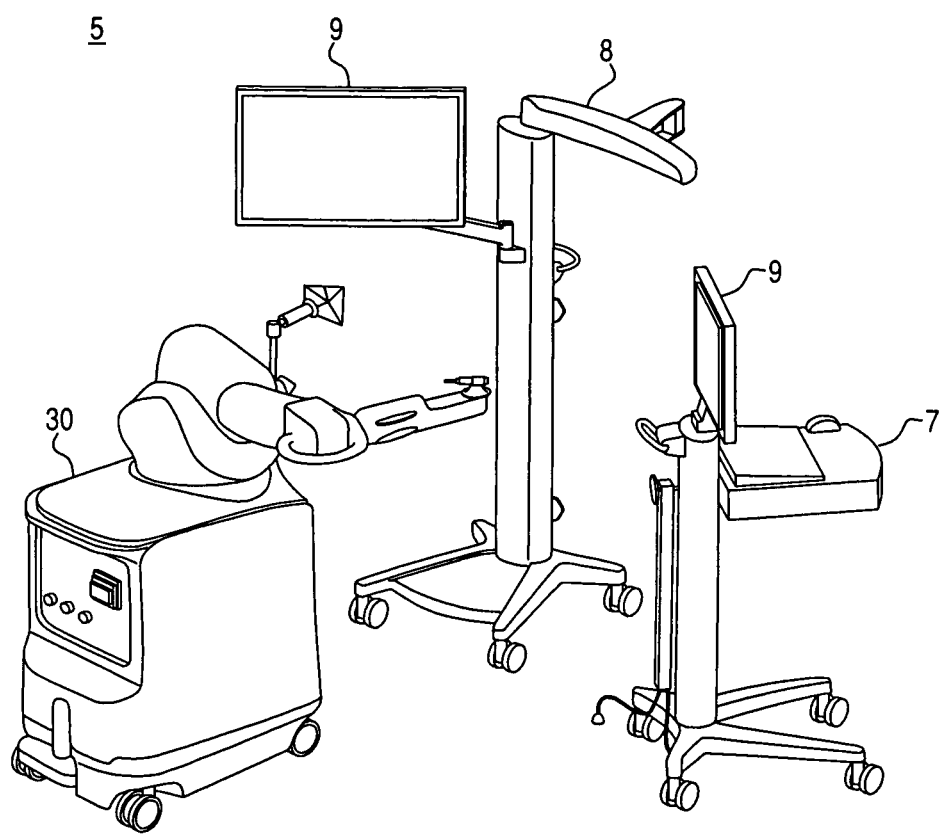
FIG. 3A is a perspective view of an embodiment of a surgical system.

A surgical system can be configured according to the present invention to perform hip replacement, as well as other surgical procedures. As shown in FIG. 3A, an embodiment of a surgical system 5 for surgical applications according to the present invention includes a computer assisted navigation system 7, a tracking device 8, a display device 9 (or multiple display devices 9), and a robotic arm 30.

Figure 3B:
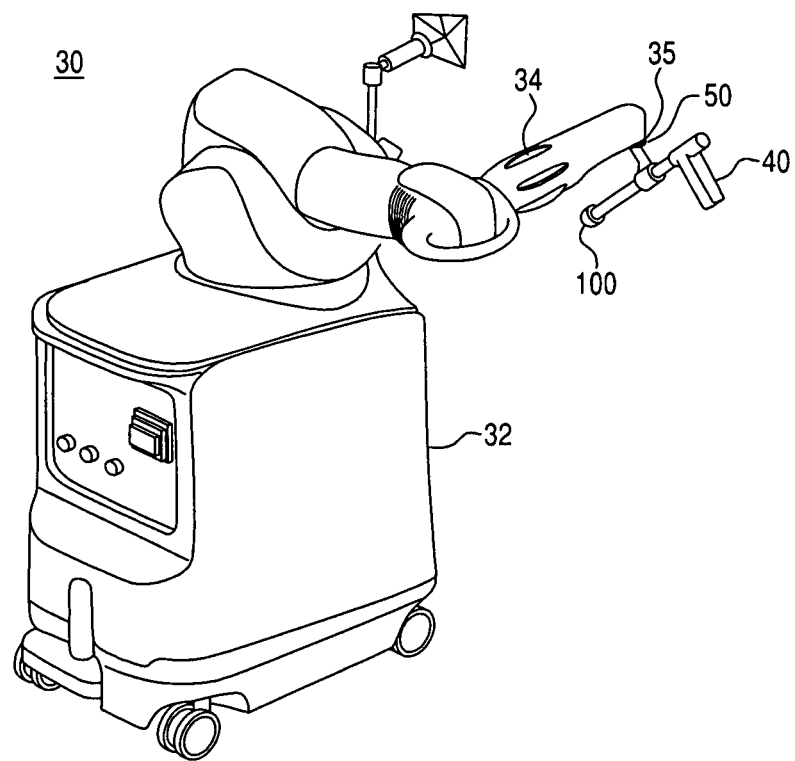
FIG. 3B is a perspective view of an embodiment of a robotic arm of the surgical system of FIG. 3A.

The robotic arm 30 can be used in an interactive manner by a surgeon to perform a surgical procedure on a patient, such as a hip replacement procedure. As shown in FIG. 3B, the robotic arm 30 includes a base 32, an articulated arm 34, a force system (not shown), and a controller (not shown). A surgical tool (e.g., an end effector 40 having an operating member) is coupled to the articulated arm 34, and the surgeon manipulates the surgical tool by grasping and manually moving the articulated arm 34 and/or the surgical tool.

The force system and controller are configured to provide control or guidance to the surgeon during manipulation of the surgical tool. The force system is configured to provide at least some force to the surgical tool via the articulated arm 34, and the controller is programmed to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. patent application Ser. No. 11/357,197 (Pub. No. US 2006/0142657), filed Feb. 21, 2006, and/or U.S. patent application Ser. No. 12/654,591, filed Dec. 22, 2009, each of which is hereby incorporated by reference herein in its entirety. In a preferred embodiment the surgical system is the RIO® Robotic Arm Interactive Orthopedic System manufactured by MAKO Surgical Corp. of Fort Lauderdale, Fla. The force system and controller are preferably housed within the robotic arm 30.

The tracking device 8 is configured to track the relative locations of the surgical tool (coupled to the robotic arm 34) and the patient's anatomy. The surgical tool can be tracked directly by the tracking device 8. Alternatively, the pose of the surgical tool can be determined by tracking the location of the base 32 of the robotic arm 30 and calculating the pose of the surgical tool based on joint encoder data from joints of the robotic arm 30 and a known geometric relationship between the surgical tool and the robotic arm 30. In particular, the tracking device 8 (e.g., an optical, mechanical, electromagnetic, or other known tracking system) tracks (or enables determination of) the pose (i.e., position and orientation) of the surgical tool and the patient's anatomy so the navigation system 7 knows the relative relationship between the tool and the anatomy.

In operation, a user (e.g., a surgeon) manually moves the robotic arm 30 to manipulate the surgical tool (e.g., the end effector 40 having an operating member) to perform a surgical task on the patient, such as bone cutting or implant installation. As the surgeon manipulates the tool, the tracking device 8 tracks the location of the surgical tool and the robotic arm 30 provides haptic (or force) feedback to limit the surgeon's ability to move the tool beyond a predefined virtual boundary that is registered (or mapped) to the patient's anatomy, which results in highly accurate and repeatable bone cuts and/or implant placement. The robotic arm 30 operates in a passive manner and provides haptic feedback when the surgeon attempts to move the surgical tool beyond the virtual boundary. The haptic feedback is generated by one or more actuators (e.g., motors) in the robotic arm 30 and transmitted to the surgeon via a flexible transmission, such as a cable drive transmission. When the robotic arm 30 is not providing haptic feedback, the robotic arm 30 is freely moveable by the surgeon and preferably includes a virtual brake that can be activated as desired by the surgeon. During the surgical procedure, the navigation system 7 displays images related to the surgical procedure on one or both of the display devices 9.

End Effector

Figure 4A:
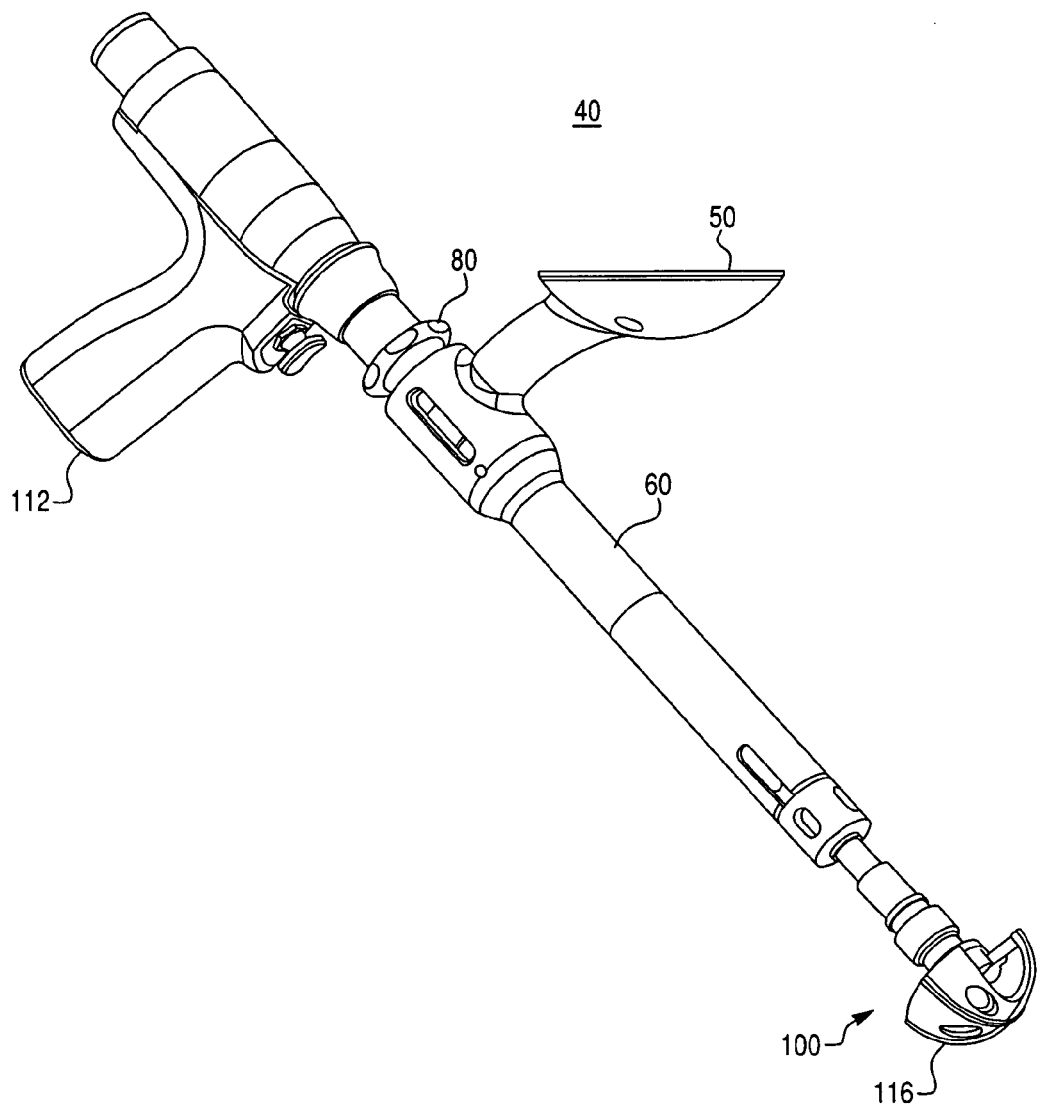
FIG. 4A is a perspective view of an embodiment of an end effector coupled to an embodiment of an operating member.
Figure 4B:
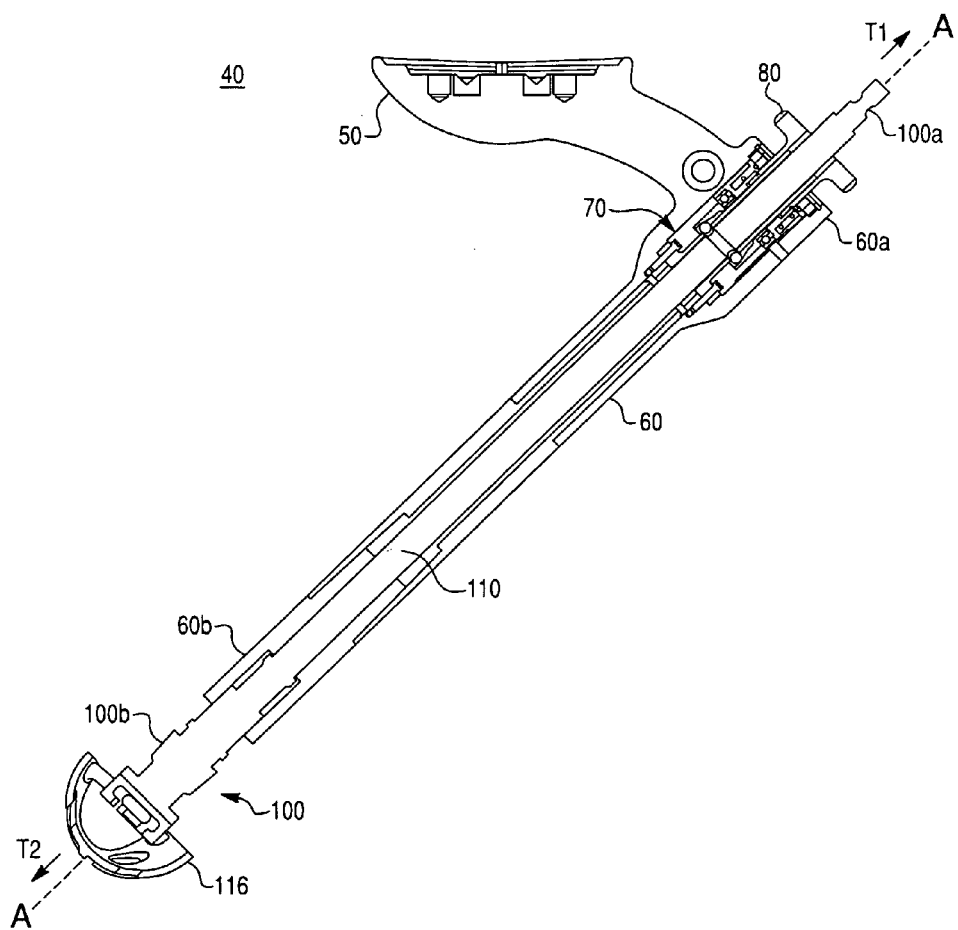
FIG. 4B is a cross-sectional view of the end effector and operating member of FIG. 4A.
Figure 4C:
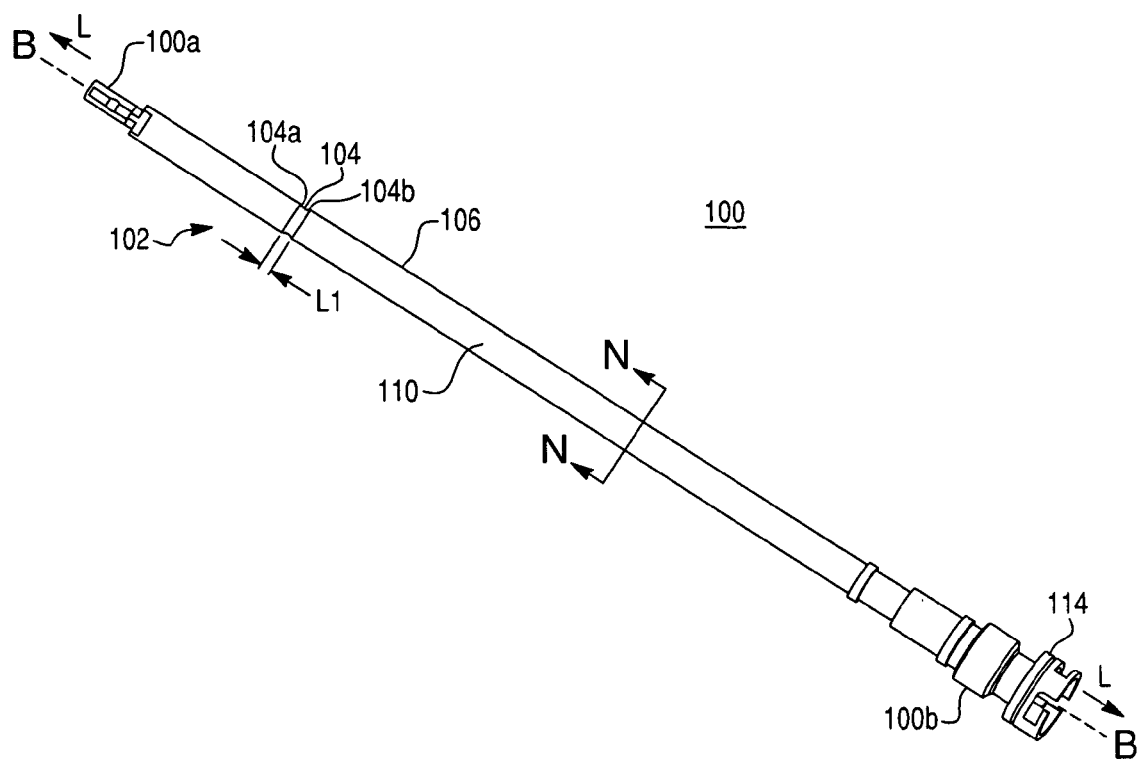
FIG. 4C is a perspective view of a shaft of the operating member of FIG. 4A.

A surgical tool has been developed that can be configured, for example, to work with the robotic arm 30 while allowing modification and performance of different functions. FIGS. 4A-4C show an embodiment of a surgical tool according to the present invention. In this embodiment, the tool is an end effector 40 configured to be mounted to an end of the robotic arm 30. The end effector 40 includes a mounting portion 50, a housing 60, a coupling device 70, and a release member 80. The end effector 40 is configured to individually and interchangeably support and accurately position multiple operating members relative to the robotic arm 30. In FIGS. 4A-4C, the end effector 40 is coupled to an operating member 100.

The mounting portion (or mount) 50 preferably couples the end effector 40 to the robotic arm 30. In particular, the mounting portion 50 extends from the housing 60 and is configured to couple the end effector 40 to a corresponding mounting portion 35 of the robotic arm 30 using, for example, mechanical fasteners, such that the mounting portions are fixed relative to one another. The mounting portion 50 can be attached to the housing 60 or formed integrally with the housing 60 and is configured to accurately and repeatably position the end effector 40 relative to the robotic arm 30. In one embodiment, the mounting portion 50 is a semi-kinematic mount as described in U.S. patent application Ser. No. 12/644,964, filed Dec. 22, 2009, and hereby incorporated by reference herein in its entirety.

Figure 10A:
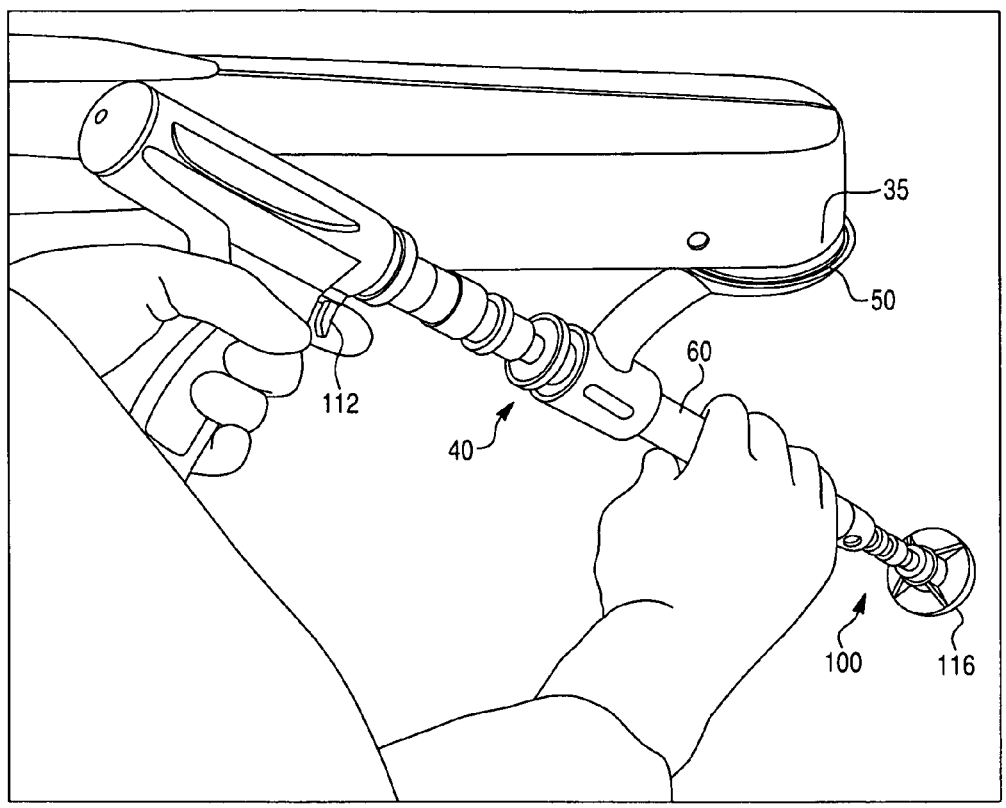
FIG. 10A illustrates how a surgeon holds the end effector and operating member of FIG. 4A for a reaming an acetabulum of a patient.
Figure 10B:
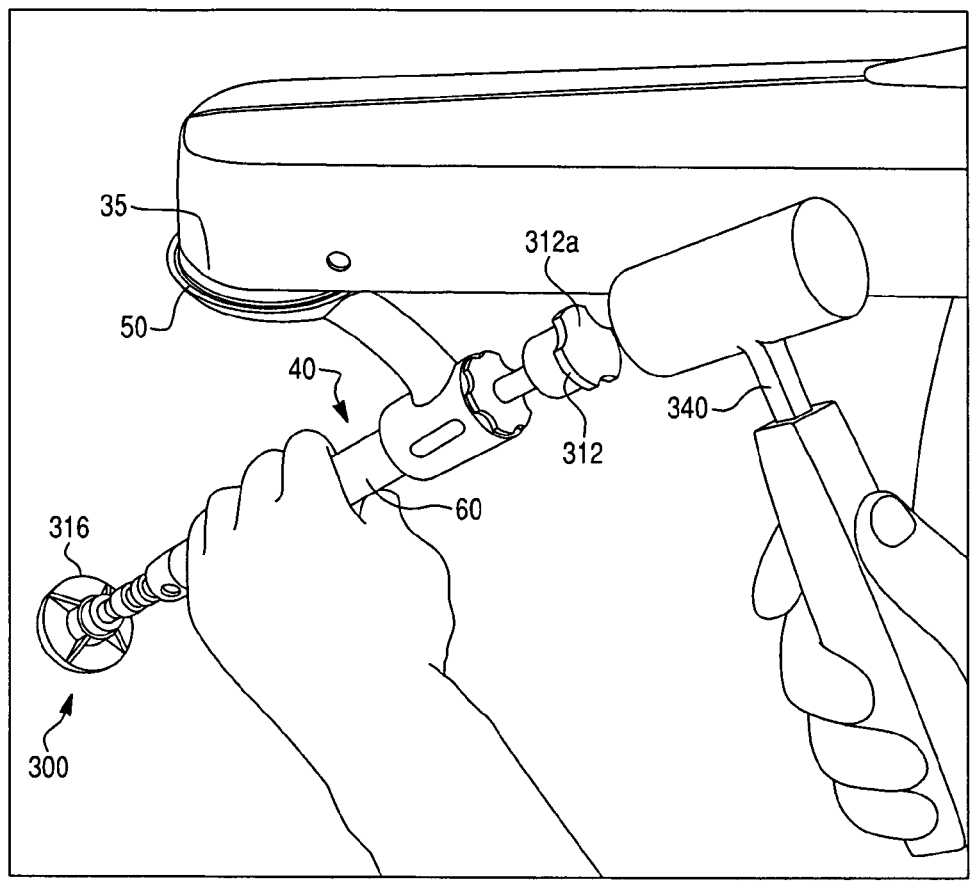
FIG. 10B illustrates how a surgeon uses the end effector and operating member of FIG. 7A to impact an acetabular cup into a reamed acetabulum of a patient.

The housing 60 is configured to receive the operating member 100 and to provide a user interface for the surgeon. For example, as shown in FIGS. 10A and 10B, the surgeon grasps the housing 60 to manipulate the end effector 40 to perform a task with the operating member 100. In this embodiment, the housing 60 is a hollow elongated cylinder having a central axis A-A, a proximal end 60a, and a distal end 60b.

Referring to FIG. 4B, to install the operating member 100 in the end effector 40, the surgeon inserts a proximal end 100a of a shaft 110 of the operating member 100 into the distal end 60b of the housing 60, slides the shaft 110 in a direction T1, and actuates the release member 80, which moves the coupling device 70 to a "release" position and enables the shaft 110 to be fully received in the housing 60. When the shaft 110 extends from the proximal end 60a of the housing 60 by an appropriate amount, the surgeon releases the release member 80, which moves the coupling device 70 to a "connect" position and couples the shaft 110 to the housing 60. Once the shaft 110 is coupled to the housing, additional equipment can be attached to the shaft 110, such as a drive motor 112, a cutting element 116, or other component of the operating member 100.

To remove the operating member 100 from the end effector 40, the surgeon removes the drive motor 112 and cutting element 116 and actuates the release member 80, which moves the coupling device 70 to the release position. The surgeon then slides the shaft 110 in a direction T2 until the operating member 100 clears the distal end 60b of the housing 60.

Figure 4D:
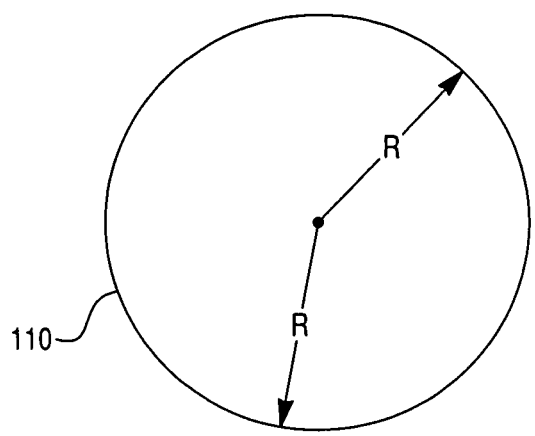
FIG. 4D is a cross sectional view of the shaft of FIG. 4C taken along line N-N.
Figure 5A:
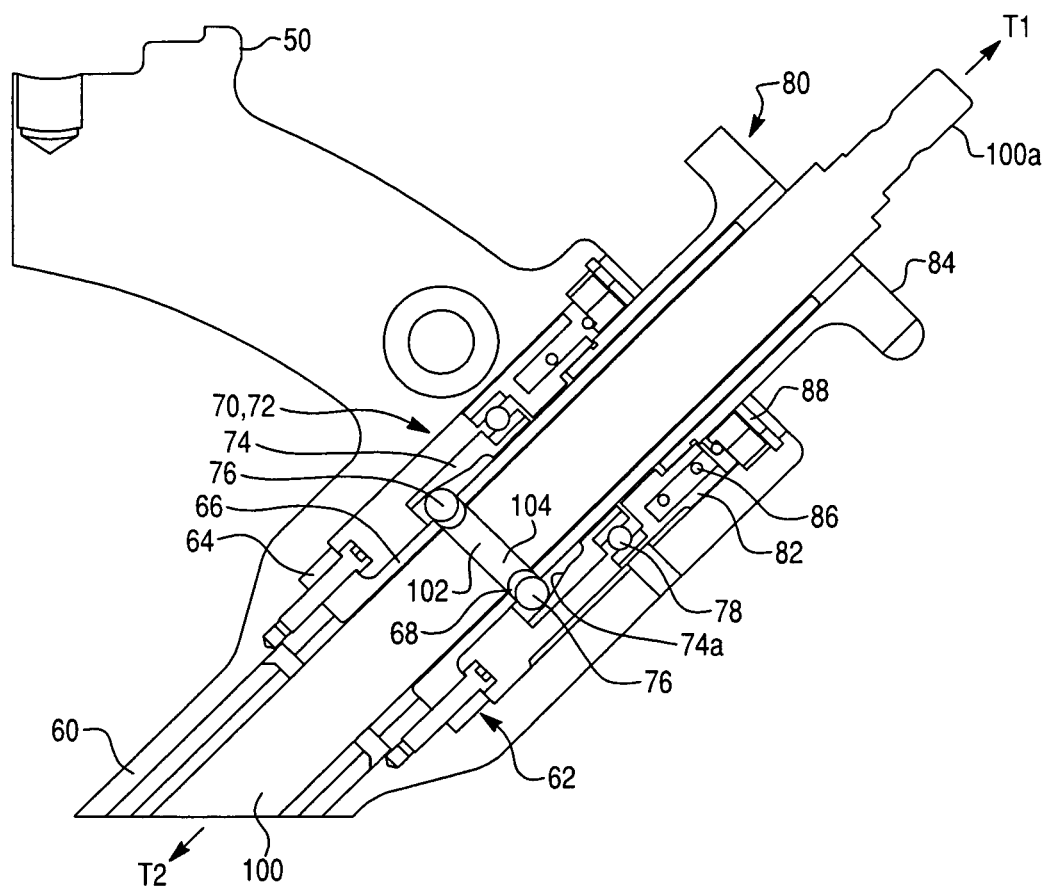
FIG. 5A is a cross-sectional view of an embodiment of a coupling device of the end effector of FIG. 4A in a release position.

The end effector 40 may include a receiving portion 62 that permits only desired movement of the operating member 100. The receiving portion 62 is disposed within the housing 60. The receiving portion 62 is configured to receive at least a portion of the operating member 100 so as to permit rotation of the operating member 100 relative to the housing 60 while constraining movement of the operating member 100 in a radial direction R of the operating member 100 (shown in FIG. 4D). For example, as shown in FIGS. 5A and 5C, the receiving portion 62 includes a flange 64 that is affixed to the housing 60 (e.g., using mechanical fasteners) and a cylindrical portion 66 through which the operating member 100 extends. Although the receiving portion 62 is fixed relative to the housing 60 via the flange 64, the operating member 100 is not connected to the receiving portion 62 (e.g., via mechanical fasteners, an interference fit, or the like) and thus can rotate and translate relative to the receiving portion 62 and the housing 60. Because the operating member 100 extends through the cylindrical portion 66, however, the operating member 100 is constrained by the cylindrical portion 66 and prevented from moving in the radial direction R. The receiving portion 62 also includes at least one hole 68 that enables the coupling device 70 to engage the operating member 100 as described below.

The coupling device 70 of the end effector can be used to provide constraints on longitudinal movement of the operating member. The coupling device 70 is disposed on the housing 60 and configured to couple the operating member 100 to the housing 60 so as to permit rotation of the operating member 100 relative to the housing 60. In one embodiment, the coupling device 70 includes a retaining member 72. As described below, the retaining member 72 is configured to engage the operating member 100 to constrain movement of the operating member 100 relative to the housing 60 in a longitudinal direction L of the operating member 100 (shown in FIG. 4C) while permitting rotation of the operating member 100.

Figure 5B:
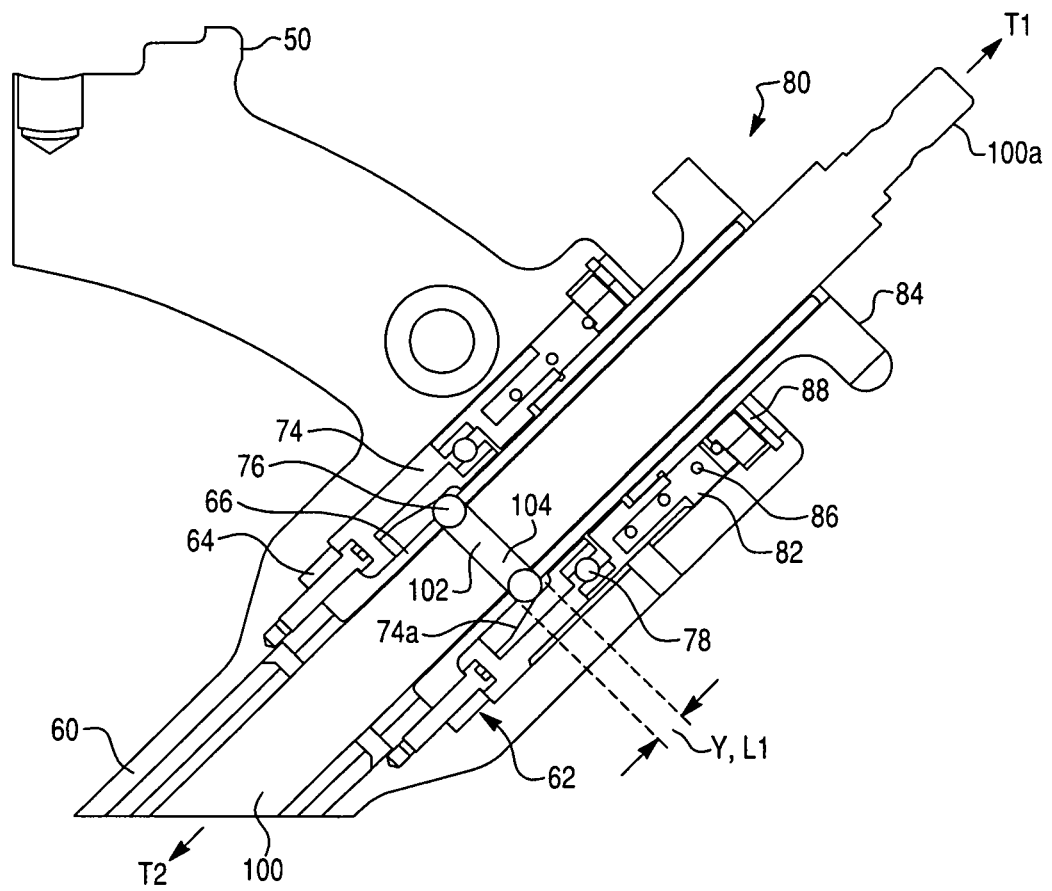
FIG. 5B is a cross-sectional view of the coupling device of FIG. 5A in a connect position.
Figure 5C:
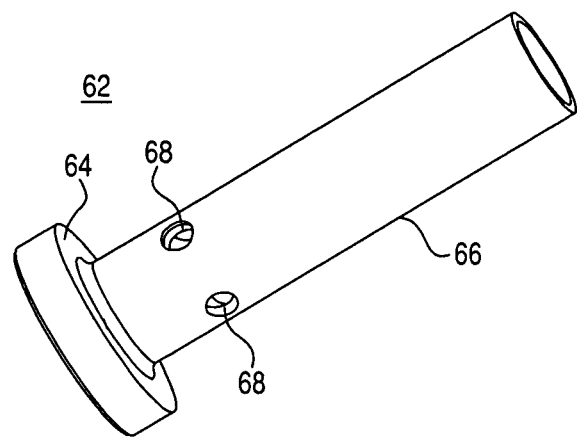
FIG. 5C is a perspective view of an embodiment of a receiving portion of the end effector of FIG. 4A.

As shown in FIGS. 5A-5C, the retaining member 72 includes a first portion 74 and a second portion 76. The first portion 74 is configured to translate in the longitudinal direction L and to rotate relative to the housing 60. For example, as shown in FIG. 5A, the first portion 74 is coupled to the release member 80 via a bearing 78 (e.g., a ball bearing). The first portion 74 is rigidly fixed to an inner race of the bearing 78 while an outer race of the bearing 78 is rigidly fixed to a slide member 82 of the release member 80, thus enabling the first portion 74 to rotate with low friction relative to the housing 60. The slide member 82 is connected to a knob 84 of the release member 80 and can translate in the longitudinal direction L. A compression spring 86 is disposed between the slide member 82 and a spring retainer 88 that is rigidly fixed to the housing 60. The compression spring 86 biases the slide member 82 and knob 84 toward a forward position (the connect position shown in FIG. 5B). When the surgeon actuates the knob 84 by pulling the knob 84 back away from the housing 60 in the direction T1 (into the release position shown in FIG. 5A), the slide member 82 moves with the knob 84 and compresses the compression spring 86. Because the first portion 74 is coupled to the slide member 82 via the bearing 78, the first portion 74 also translates along the longitudinal direction L when the knob 84 is moved into the release position. In this manner, the release member 80 is coupled to the coupling device 70 and configured to move the retaining member 72 between the connect position and the release position.

Figure 5D:
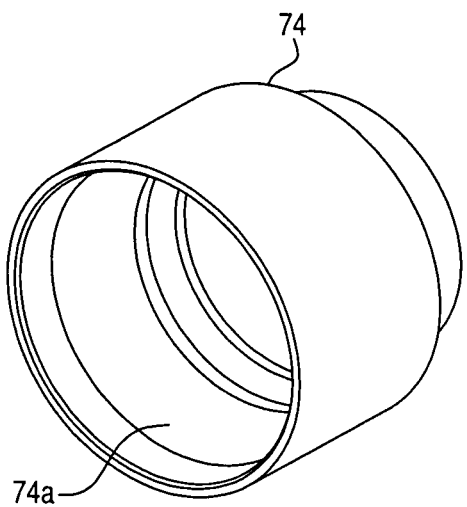
FIG. 5D is a perspective view of an embodiment of a retaining member of the coupling device of FIG. 5A.
Figure 5E:
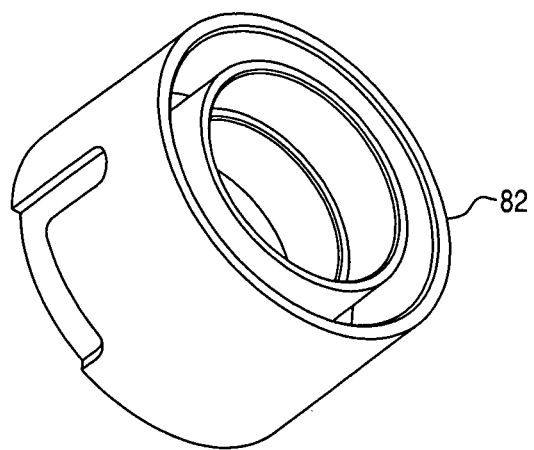
FIG. 5E is a perspective view of a slide member of the coupling device of FIG. 5A.

The second portion 76 of the retaining member 72 is configured to move along the radial direction R in response to movement of the first portion 74 along the longitudinal direction L. As shown in FIGS. 5A and 5B, the first portion 74 is disposed outward relative to the receiving portion 62 of the housing 60 and includes a surface 74a configured to engage the second portion 76 and displace the second portion 76 in the radial direction R as the first portion 74 moves from a first position (the release position shown in FIG. 5A) to a second position (the connect position shown in FIG. 5B). In one embodiment, as shown in FIG. 5D, the first portion 74 is hollow cylinder, and the surface 74a is an inclined inner surface of the cylinder. The first portion 74 is oriented relative to the housing 60 such that the surface 74 inclines (i.e., an inner radius of the first portion 74 decreases) in the direction T1. In this embodiment, the second portion 76 comprises at least one ball bearing that is aligned with the hole 68 of the receiving portion 62. Preferably, the second portion 76 includes multiple ball bearings (e.g., four), each aligned with a corresponding hole 68 on the receiving portion 62. Because the surface 74a is inclined, the surface 74a presses the ball bearings radially inward as the first portion 74 moves from the release position (FIG. 5A) to the connect position (FIG. 5B). Each ball bearing moves inward in the corresponding hole 68 along the radial direction R to engage a portion of the operating member 100.

The operating member 100 cooperates with the coupling device 70 to maintain the constraints on longitudinal movement. The operating member 100 includes a coupling region 102. When the coupling region 102 is aligned with the holes 68 and the coupling device 70 is moved to the connect position, the coupling device 70 is adapted to constrain movement of the operating member 100 in the longitudinal direction L to a region of constraint Y (shown in FIG. 5B). In this embodiment, the coupling region 102 is a recess 104 in a peripheral surface 106 of the operating member 100. As shown in FIG. 4C, the recess 104 has a proximal end 104a and a distal end 104b. The proximal and distal ends 104a, 104b define a range of motion of the operating member 100 in the region of constraint Y. For example, when the ball bearings move radially inward into the holes 68, they engage the recess 104 as shown in FIG. 5B. When the coupling device 70 is in the connect position, the ball bearings are captured between the surface 74a and the recess 104 and are therefore prevented from moving in the radial direction R. Similarly, because the ball bearings are received in the holes 68, they are constrained from moving in the longitudinal direction L. Although the ball bearings are captured, they are free to rotate in a manner similar to ball bearings in the bearing 78. Thus, the surface 74a functions as an outer race of a ball bearing while the recess 104 functions as an inner race of a ball bearing. In this manner, the ball bearings (i.e., the second portion 76 of the retaining member 72) are configured to rotate relative to both the operating member 100 and the first portion 74 of the retaining member 72. In the connect position, when the ball bearings are engaged with the recess 104, the ball bearings interact with (i.e., contact) the proximal end 104a and/or the distal end 104b of the recess 104 to constrain longitudinal movement of the operating member 100. In this embodiment, a longitudinal length L1 of the recess 104 is sized such that the proximal and distal ends 104a, 104b simultaneously contact the ball bearings when the ball bearings are engaged with the first coupling region 102 in the connect position. As a result, the operating member 100 is substantially constrained from moving in the longitudinal direction L.

As described above, both the first and second portions 74, 76 of the retaining member 72 can rotate freely, and the first portion 74 is slidable within the housing 60. In this manner, the retaining member 72 is configured to rotate relative to the housing 60 and relative to the operating member 100 and to move axially along the axis A-A of the housing 60. Additionally, the retaining member 72 is configured to be moveable between first and second positions (the connect and release positions) and is configured to constrain the operating member 100 when the retaining member 72 is in the first position (the connect position of FIG. 5B) and permit decoupling of the operating member 100 from the housing 60 when the retaining member 72 is in the second position (the release position of FIG. 5A).

In the embodiment of FIGS. 4A-5B, the operating member 100 is a reamer for resurfacing the acetabulum 22 during a hip replacement procedure. The operating member 100 includes the shaft 110 with proximal and distal ends 100a, 100b. The proximal end 100a is configured to engage the drive motor 112. The distal end 100b is a workpiece-engaging end that includes an attachment mechanism 114 that engages the cutting element 116 that is configured to cut bone. In operation (as shown in FIG. 10A), the surgeon actuates the drive motor 112 with one hand and grasps the end effector 40 with the other hand to maneuver the end effector 40. The drive motor 112 imparts rotational motion to the operating member 100 and the cutting element 116. As described further below in connection with step S8 of FIG. 11, the surgeon positions the operating member 100 relative to the acetabulum 22 in accordance with a surgical plan and reams the surface of the acetabulum 22 with the rotating cutting element 116. When the rotating cutting element 116 contacts the acetabulum 22, the surface of the acetabulum 22 (e.g., diseased bone) is cut away or resurfaced.

Figure 6A:
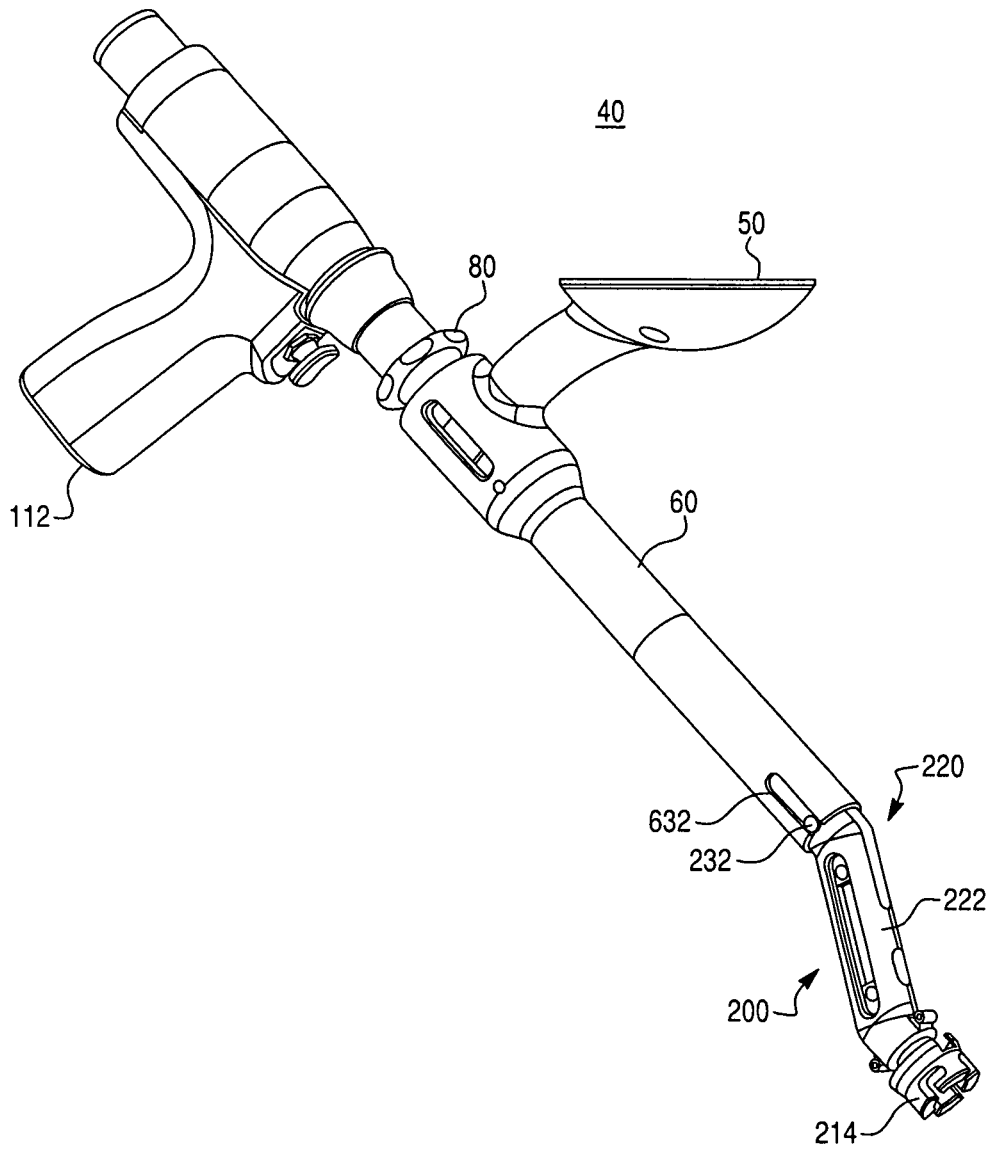
FIG. 6A is a perspective view of the end effector of FIG. 4A coupled to another embodiment of an operating member.
Figure 6B:
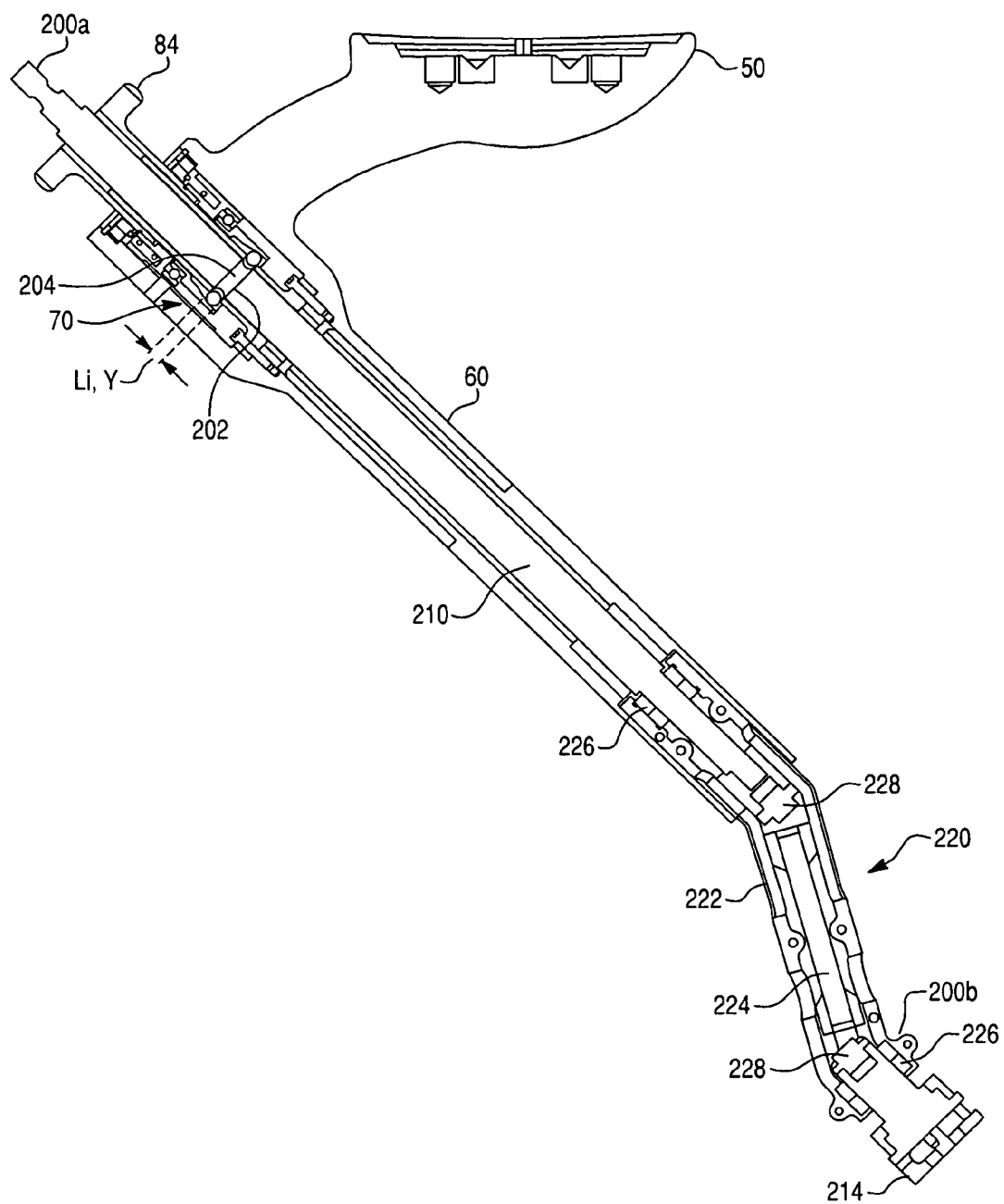
FIG. 6B is a cross-sectional view of the end effector and operating member of FIG. 6A.
Figure 6C:
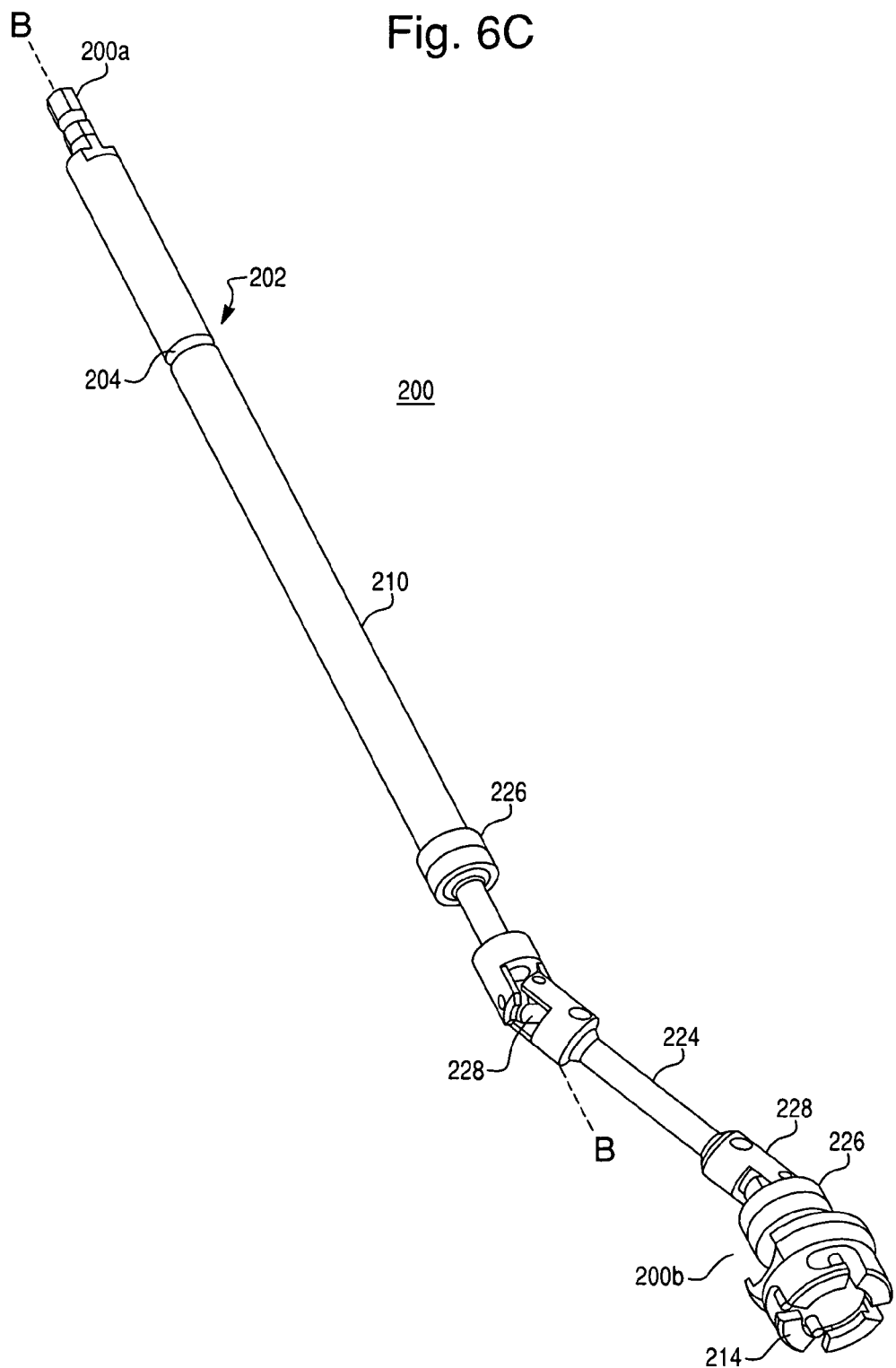
FIG. 6C is a perspective view of a shaft of the operating member of FIG. 6A.

To provide flexibility to the surgeon, the end effector 40 is configured such that the operating member 100 can be interchanged with other operating members. For example, the operating member 100 can be interchanged with an operating member 200. In one embodiment, the operating member 200 is an offset reamer. As is well known, an offset reamer might be preferred over a straight reamer by a surgeon using an antero-lateral approach as opposed to a postero-lateral approach. In this embodiment, the operating member 200 is identical to the operating member 100 except the operating member 200 includes an offset portion 220. For example, as shown in FIGS. 6A-6C, the operating member 200 includes a proximal end 200a configured to engage the drive motor 112 and a distal end 200b that includes an attachment mechanism 214 that engages a cutting element (not shown) that is identical or similar to the cutting element 116. The offset portion 220 is connected to a shaft 210 and includes an offset shaft 224 having universal joints 228. The offset shaft 224 is enclosed by a support housing 222, and duplex pair ball bearings 226 enable the offset shaft 224 to rotate relative to the support housing 222 with low friction. The offset portion 220 also includes an anti-rotation pin 232 that engages a corresponding slot 632 in the housing 60 of the end effector 40. The anti-rotation pin 232 ensures the offset portion 220 is correctly assembled to the end effector 40 and prevents rotation of the support housing 222 relative to the housing 60 when torque is applied by the drive motor 112. The operating member 200 is coupled to the end effector 40 via the coupling device 70 in a manner identical to the operating member 100. In particular, the operating member 200 includes a coupling region 202 having a recess 204 that engages the coupling device 70 of the end effector 40 in the same manner described above in connection with the operating member 100. In operation, the surgeon couples the shaft 210 of the operating member 200 to the end effector 40 (as described above in connection with the operating member 100), attaches the knob 84, the drive motor 112, and the cutting element 116 to the shaft 210, and operates the operating member 200 in the same manner as the operating member 100.

The end effector 40 is also configured to be used individually and interchangeably with multiple operating members having different functions. For example, a first operating member can be configured to have a first function, and a second operating member can be configured to have a second function. In one embodiment, the first operating member is the operating member 100 (shown in FIGS. 4A-5B) or the operating member 200 (shown in FIGS. 6A-6C) having a reaming function, and the second operating member is an operating member 300 (shown in FIGS. 7A-8B) having an impaction function. In this embodiment, the operating member 300 is a straight impactor for implanting an acetabular cup (e.g., the acetabular cup 28a) into a prepared acetabulum. Alternatively, the second operating member could be an operating member 400 (shown in FIGS. 9A and 9B), such as an offset impactor. The operating member 300 is similar to the operating member 100 except the operating member 300 is configured to engage with a prosthetic component 316 (e.g., the acetabular cup 28a) instead of a cutting element and an impactor head 312 instead of a drive motor. Additionally, the operating member 300 is configured to translate in the directions T1, T2 relative to the end effector 40. Specifically, the operating member 300 is configured to translate relative to the coupled mounting portions 35, 50 when the surgeon applies an impact force to the impactor head 312.

The operating member 300 includes a shaft 310 having a proximal end 300a and a distal end 300b. The distal end 300b is a workpiece-engaging end configured to couple to the prosthetic component 316 (e.g., via screw threads). The proximal end 300a is configured to withstand an impact force sufficient to impact the prosthetic device 316 into the hip joint 10 of the patient. For example, the proximal end 300a is configured to engage the impactor head 312 using any suitable mechanism (e.g., screw threads, mechanical fasteners, a key way, or the like). As is well known, the impactor head 312 provides a surface 312a that the surgeon strikes (e.g., with a mallet 340) to impart force to the operating member 300. The impactor head 312 can also be grasped by the surgeon and used to rotate the operating member 300 to screw the prosthetic component 316 onto and off of the distal end 300b.

Figure 8A:
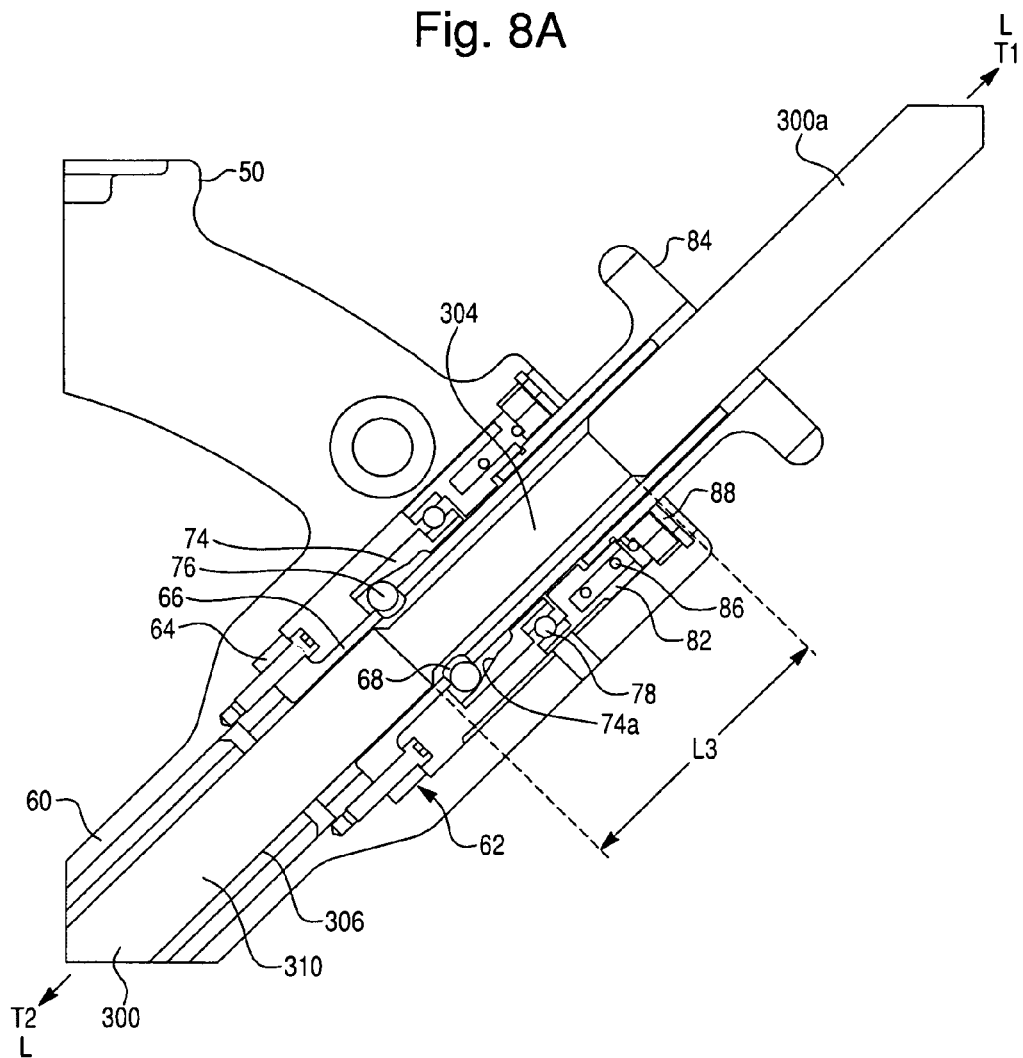
FIG. 8A is a cross-sectional view of the coupling device of the end effector of FIG. 7A in a release position.
Figure 8B:
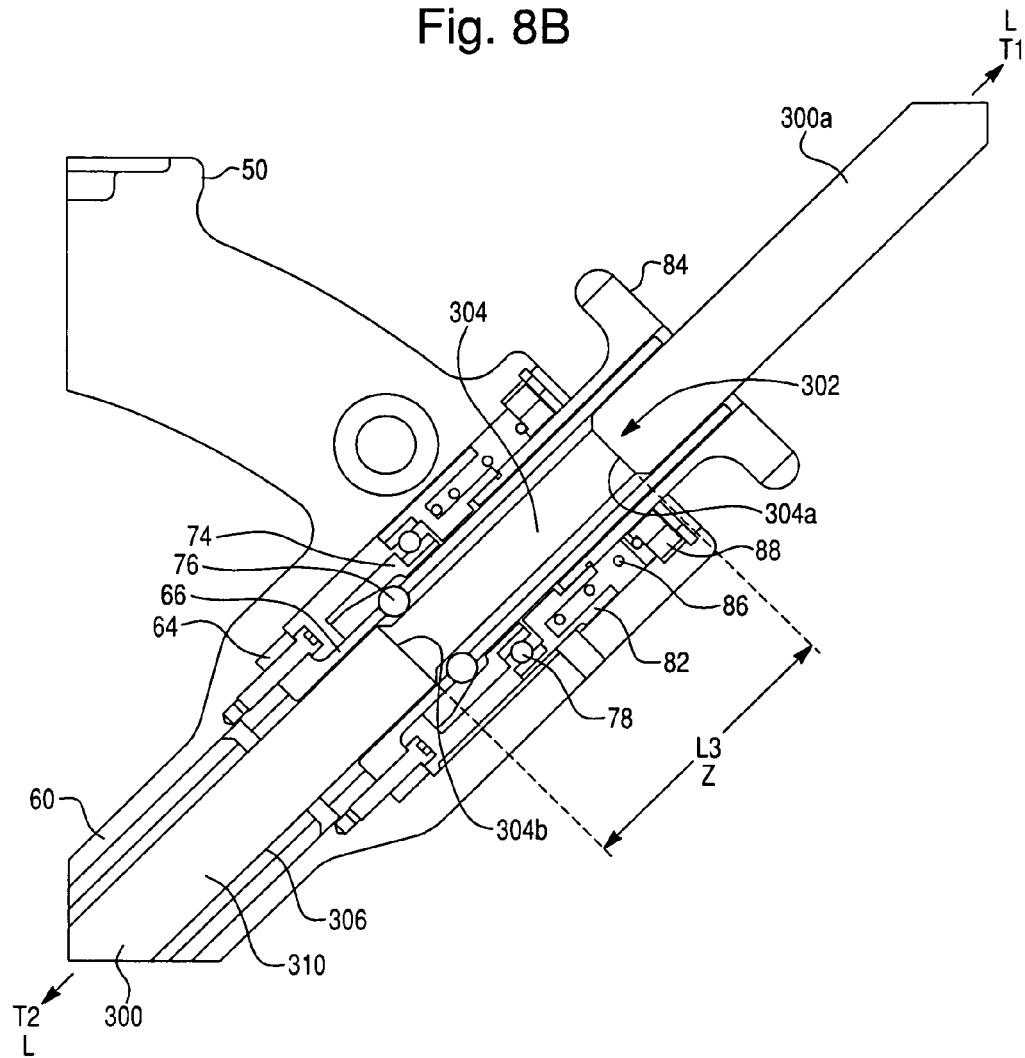
FIG. 8B is a cross-sectional view of the coupling device of FIG. 8A in a connect position.

The operating member 300 is coupled to the end effector 40 via the coupling device 70 in a manner identical to that described above in connection with the operating member 100 except the operating member 300 is configured to translate relative to the end effector 40 when the coupling device 70 is in the connect position. For example, as shown in FIGS. 8A and 8B, the operating member 300 includes a coupling region 302 that engages the coupling device 70 of the end effector 40. In a manner identical to the coupling region 102 of the first operating member 100, when the coupling region 302 is aligned with the holes 68 of the receiving portion 62 and the coupling device 70 is moved to the connect position (shown in FIG. 8B), the coupling device 70 constrains movement of the operating member 100 in the longitudinal direction L to a region of constraint Z (shown in FIG. 8B). For example, the coupling region 302 includes a recess 304 in a peripheral surface 306 of the shaft 310. The recess 304 has a proximal end 304a and a distal end 304b. The proximal and distal ends 304a, 304b define a range of motion of the operating member 300 in the region of constraint Z. FIG. 8A shows the coupling device 70 in the release position. When the coupling device 70 moves to the connect position (shown in FIG. 8B), the ball bearings (i.e., the second portion 76) of the retaining member 72 move radially inward into the holes 68 and engage the recess 304. When the ball bearings are engaged with the recess 304, the ball bearings interact with (i.e., contact) the proximal end 304a and/or the distal end 304b of the recess 304 to constrain longitudinal movement of the operating member 300. In this embodiment, a longitudinal length L3 of the recess 304 is sized such that the operating member can translate within the confines of the recess 304. For example, the operating member 300 can translate in the direction T2 until the proximal end 304a of the recess 304 contacts the ball bearings thereby constraining movement of the operating member 300 in the direction T2. Similarly, the operating member 300 can translate in the direction T1 until the distal end 304b of the recess 304 contacts the ball bearings thereby constraining movement of the operating member 300 in the direction T1. The ability of the operating member 300 to translate passively in the region of constraint Z when the coupling device 70 is in the connect position advantageously allows the surgeon to strike the impactor head 312 with the mallet 340 without the force of the mallet strikes being transmitted through the end effector 40 to the robotic arm 30. In this manner, the coupling region 302 protects the robotic arm 30 from damage due to impaction forces.

As can be seen by comparing FIGS. 5B and 8B, the longitudinal length L1 of the recess 104 of the operating member 100 is less than the longitudinal length L3 of the operating member 300. The longitudinal length L1 of the recess 104 and the interaction of the proximal and distal ends 104a, 104b of the recess 104 with the retaining member 72 (i.e., the ball bearings) define the region of constraint Y. Because the proximal and distal ends 104a, 104b simultaneously contact the ball bearings when the ball bearings are engaged with the first coupling region 102 in the connect position, the region of constraint Y is a substantially fixed axial location relative to the housing 60. As a result, the operating member 100 is substantially constrained from moving in the longitudinal direction L (i.e., the directions T1, T2) when the coupling device 70 is in the connect position. In contrast, the region of constraint Z of the operating member 300 permits translation of the operating member 300. For example, the longitudinal length L3 of the recess 304 and the interaction of the proximal and distal ends 304a, 304b of the recess 304 with the retaining member 72 (i.e., the ball bearings) define the region of constraint Z. Because the recess 304 is elongated, the ball bearings (of the retaining member 72) contact the proximal end 304a of the recess 304, the distal end 304b of the recess 304, or neither when the coupling device 70 is in the connect position (i.e., when the retaining member 72 is engaged with the coupling region 302). As a result, the region of constraint Z includes a first axial location (i.e., a location where the proximal end 304a of the recess 304 contacts the ball bearings) and a second axial location (i.e., a location whether the distal end 304b of the recess 304 contacts the ball bearings), and the operating member 300 is moveable therebetween. In this manner, the coupling device 70 and the operating members 100, 300 are configured to constrain the movement of the received operating member in the longitudinal direction L to a first region of constraint Y when the coupling device 70 engages the coupling region 102 of the operating member 100 and to a second region of constraint Z, which is different from the first region of constraint Y, when the coupling device 70 engages the coupling region 302 of the operating member 300.

Figure 7B:
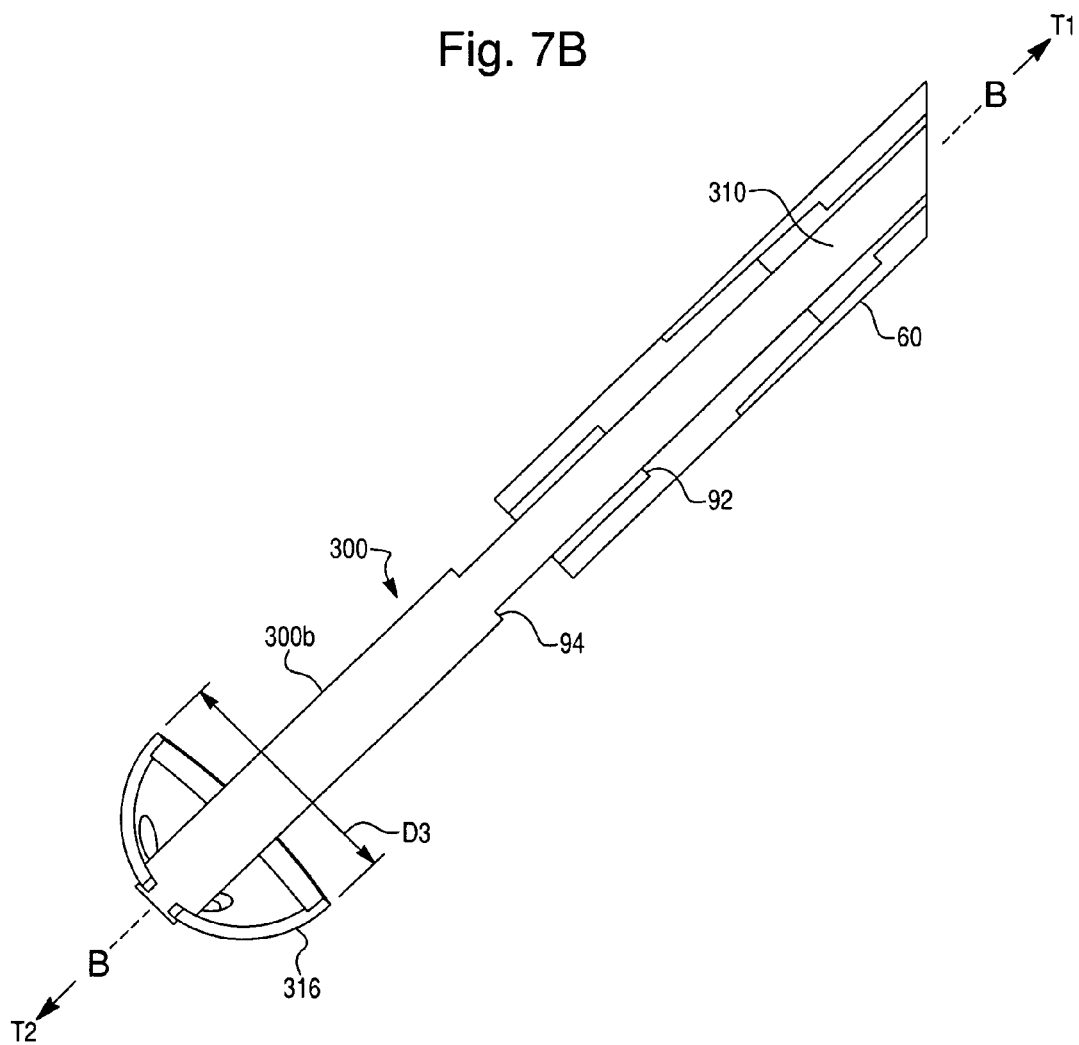
FIG. 7B is a cross-sectional view of the end effector and operating member of FIG. 7A in an extended position.

The end effector 40 may also include a stop member 90 that is configured to engage an operating member to limit movement of the operating member relative to the housing 60 and to provide an accurate axial location of the operating member 300 relative to the end effector 40. For example, as shown in FIGS. 7A and 7B, the stop member 90 includes a locating surface 92 (e.g., a counterbore) disposed within the housing 60 of the end effector 40 and a corresponding locating surface 94 (e.g., a shoulder or protrusion) disposed on the shaft 310 of the operating member 300. Although the stop member 90 may be disposed in any suitable location, in this embodiment, the stop member 90 is disposed remotely from the recess 304 and the coupling device 70. In particular, the stop member 90 is closer to the distal end 300b of the operating member 300 while the recess 304 and the coupling device 70 are closer to the proximal end 300a of the operating member 300. When the locating surface 94 contacts the locating surface 92 (a seated position shown in FIG. 7A), translation of the operating member 300 in the direction T1 is prevented. In contrast, when the locating surfaces 92, 94 are not in contact (an extended position shown in FIG. 7B), the operating member 300 can translate in the direction T1 and the direction T2 within the region of constraint Z. In this manner, the stop member 90 is configured to engage the operating member 300 to limit translation of the operating member 300 in the region of constraint Z. In one embodiment, the stop member 90 is positioned so that the operating member 300 is prevented from translating within the full range of the region of constraint Z. In this embodiment, the operating member 300 translates between a first location defined by the proximal end 304a of the recess 304 and a second location defined by the locating surface 94. In this manner, the stop member 90 can be used to effectively reduce the range of travel of the operating member 300 when the coupling device 70 is in the connect position. Reducing the range of travel in this manner advantageously reduces contact stresses because the contact area between the locating surfaces 92, 94 is greater than the surface area between the ball bearings and the distal end 304b of the recess 304.

In operation, after the surgeon finishes reaming the acetabulum 22, the surgeon removes the operating member 100 (or the operating member 200) from the end effector 40. The surgeon couples the operating member 300 (or the operating member 400) to the end effector 40 (in the same manner as described above in connection with the operating member 100) and connects the prosthetic component 316 and the impactor head 312 to the operating member 300. As shown in FIG. 10B, the surgeon grasps the end effector 40 with one hand and uses the other hand to hold the mallet 340. As described further below in connection with step S10 of FIG. 11, the surgeon properly positions the prosthetic component 316 relative to the reamed acetabulum 22 and uses the mallet 340 to impart a force to the surface 312a of the impactor head 312. During impaction, the recess 304 functions as a sliding passive joint that enables the operating member 300 to translate as described above. The impaction force impacts the prosthetic component 316 onto the acetabulum 22. Between mallet strikes, the surgeon pushes the end effector 40 forward until the locating surfaces 92, 94 of the stop member 90 are in contact (shown in FIG. 7A). The surgeon continues manually impacting the prosthetic component 316 until the prosthetic component 316 is implanted on the acetabulum 22 at the planned depth. After the prosthetic component 316 is implanted, the surgeon grasps the impactor head 312 and rotates the operating member 300 to unscrew the operating member from the implanted prosthetic component 316. If the acetabular cup includes a liner (e.g., the liner 28b), the surgeon then inserts the liner into the cup.

Figure 9A:
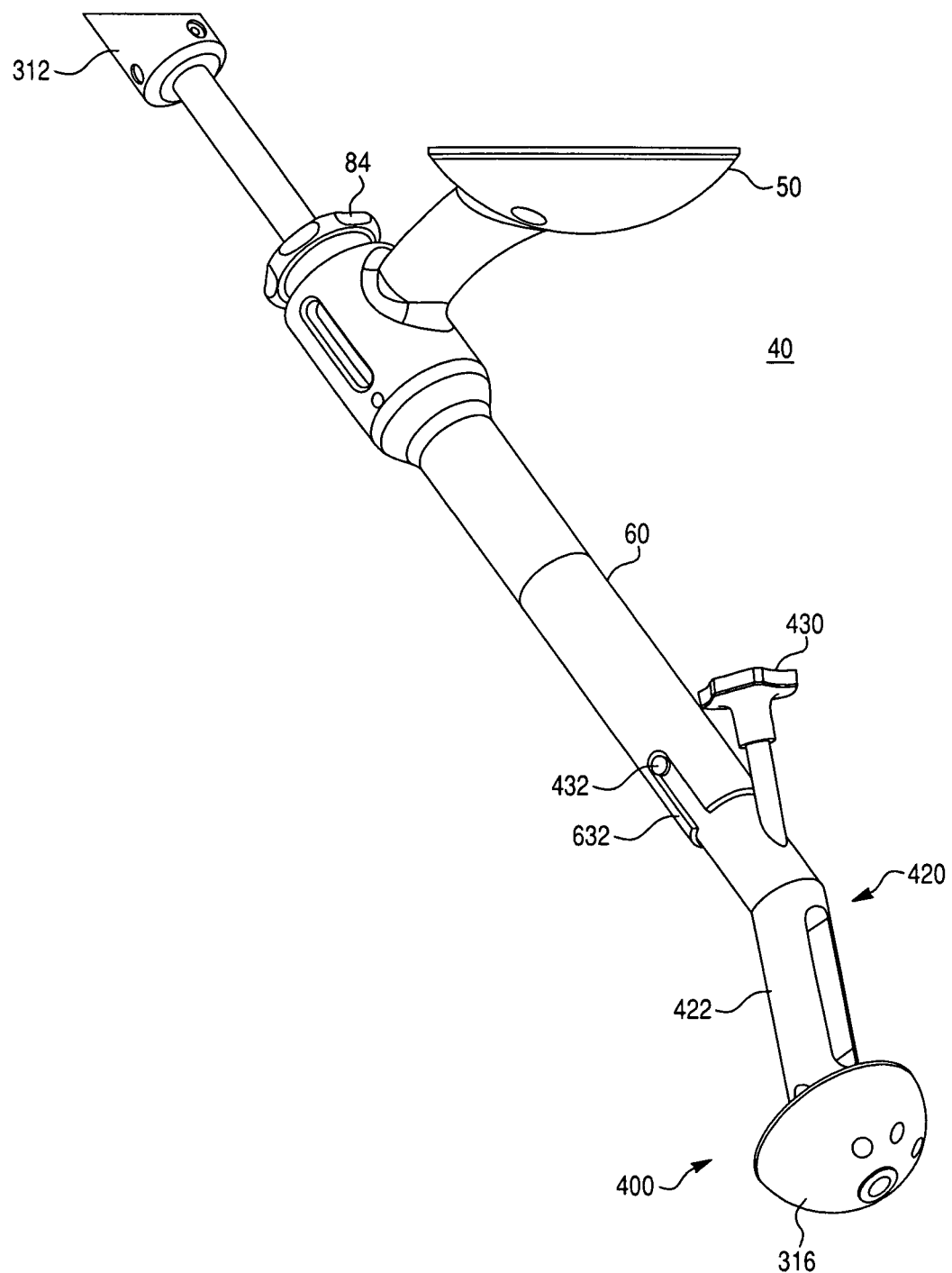
FIG. 9A is a perspective view of the end effector of FIG. 4A coupled to another embodiment of an operating member.
Figure 9B:
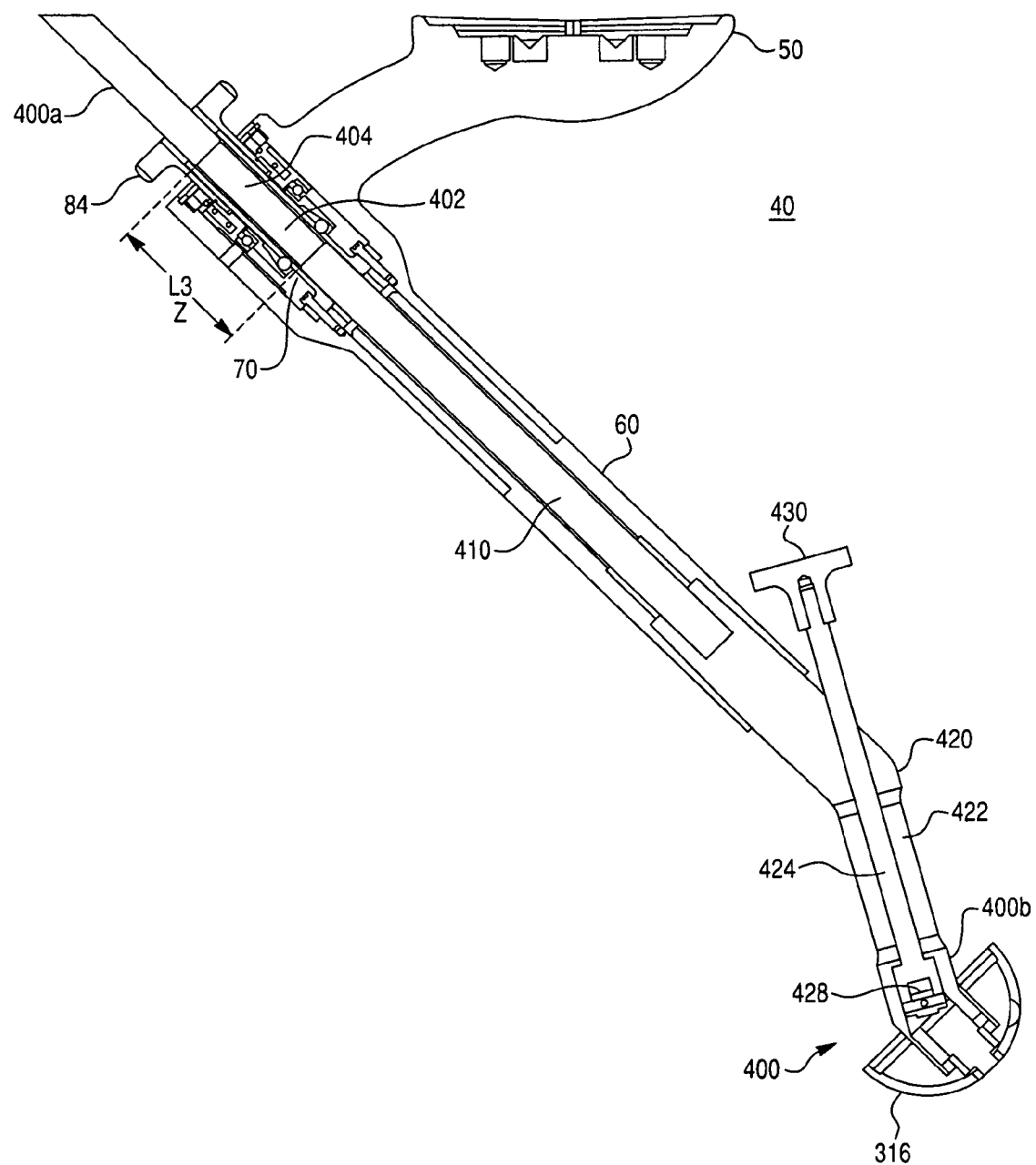
FIG. 9B is a cross-sectional view of the end effector and operating member of FIG. 9A.
Figure 11:
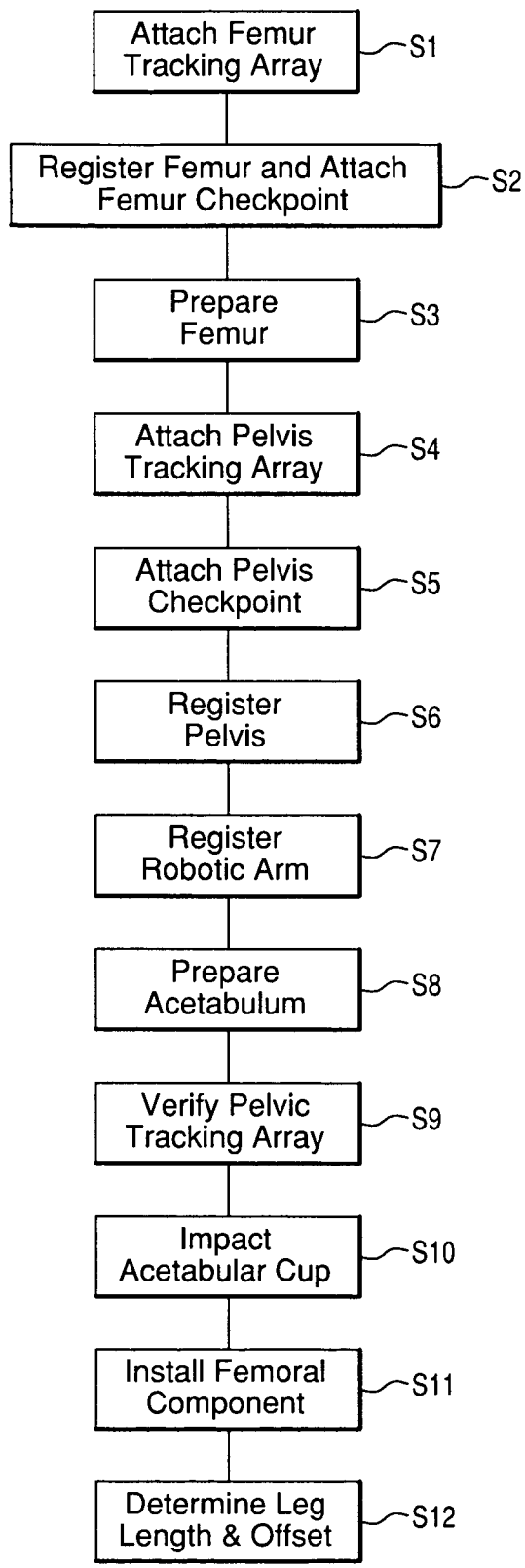
FIG. 11 illustrates an embodiment of steps of a hip replacement procedure.

Depending on the position of the patient, instead of a straight impactor (e.g., the operating member 300), the surgeon may prefer to use an offset impactor (e.g., the operating member 400). In one embodiment, the operating member 400 (shown in FIGS. 9A and 9B) is similar to the operating member 300 except the operating member 400 includes an offset portion 420. For example, as shown in FIGS. 9A and 9B, the operating member 400 includes a proximal end 400a configured to engage the impactor head 312 and a distal end 400b configured couple to the prosthetic component 316 (e.g., via screw threads). The offset portion 420 is connected to a shaft 410 and includes an offset shaft 424 having a universal joint 428 and a coupling knob 430. Because of the offset, the coupling knob 430 is used instead of the impactor head 312 to screw/unscrew the operating member 400 to/from the prosthetic component 316. An alternative embodiment could include two universal joints (e.g., similar to the offset portion 220 of the operating member 200), which would enable the impactor head 312 to be used to screw/unscrew the operating member 400 to/from the prosthetic component 316. One drawback of this alternative configuration, however, is that it can add complexity and lower the strength of the offset shaft 424. The offset shaft 424 is enclosed by a housing 422 and includes an anti-rotation pin 432. The anti-rotation pin 432 engages the corresponding slot 632 in the housing 60 to properly locate the offset portion 420 relative to the end effector 40 and to prevent rotation of the housing 422 relative to the housing 60. The operating member 400 is coupled to the end effector 40 via the coupling device 70 in a manner identical to that described above in connection with the operating member 300. In particular, the operating member 400 includes a coupling region 402 having a recess 404 that engages the coupling device 70 of the end effector 40 and enables the operating member 400 to translate longitudinally in the region of constraint Z. As shown in FIG. 11, the slot 632 is elongated thereby enabling the anti-rotation pin 432 to translate longitudinally in the slot 632 within the axial constraints of the region of constraint Z. In operation, the operating member 400 functions in the same manner as the operating member 300 except the coupling knob 430 (instead of the impactor head 312) is used to couple/decouple the prosthetic component 316 to/from the operating member 400.

Surgical Application

In operation, the surgeon can use the robotic arm 30 to facilitate a joint replacement procedure, such as reaming bone and implanting an acetabular cup for a total hip replacement or hip resurfacing procedure. As explained above, the robotic arm 30 includes a surgical tool configured to be coupled to a cutting element (for reaming) and to engage a prosthetic component (for impacting). For example, for reaming, the end effector 40 can couple to the operating member 100 or the operating member 200, each of which couples to the cutting element 116. Similarly, for impacting, the end effector 40 can couple to the operating member 300 or the operating member 400, each of which engages the prosthetic component 316. The robotic arm 30 can be used to ensure proper positioning during reaming and impacting.

FIG. 11 illustrates an embodiment of steps of a surgical procedure for performing a total hip replacement. In this embodiment, steps S1-S7, S9, S11, and S12 can be performed in any known manner, with or without robotic assistance. Steps S8 and S10 are preferably performed using the robotic arm 30. For example, step S8 (reaming) can be performed using robotic arm 30 with the end effector 40 coupled to the operating member 100 or the operating member 200, and step S10 (impacting) can be performed using the robotic arm 30 with the end effector 40 coupled to the operating member 300 or the operating member 400.

Figure 14A:
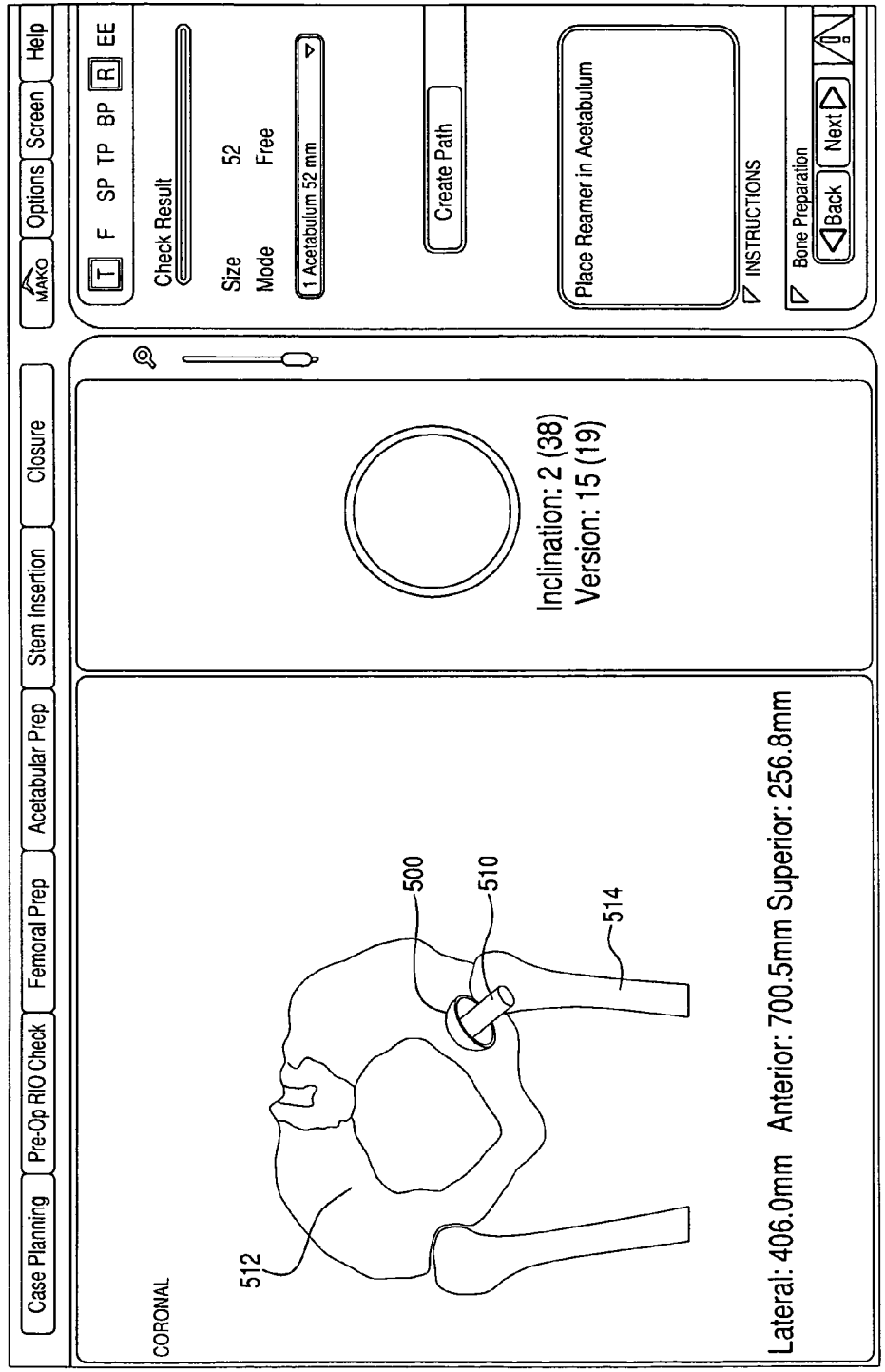

Prior to the surgical procedure, a preoperative CT scan of the patient's pelvis 12 and femur 14 is obtained. As shown in FIG. 14A, the CT scan is used to create a three dimensional model 512 of the pelvis 12 and a three dimensional model 514 of the femur 14. The three dimensional models 512, 514 are used by the surgeon to construct a surgical plan. Alternatively, X-ray images derived from the CT scan and/or the three dimensional models 512, 514 can be used for surgical planning, which may be helpful to surgeons who are accustomed to planning implant placement using actual X-ray images as opposed to CT based models. The surgeon generates a surgical plan by designating a desired pose (i.e., position and orientation) of the acetabular component 28 and the femoral component 26 relative to the models 512, 514 of the patient's anatomy. For example, a planned pose 500 of the acetabular cup 28a can be designated and displayed on a computer display, such as the display device 9. During the surgical procedure, motion of the patient's anatomy and the surgical tool in physical space are tracked by the tracking device 8, and these tracked objects are registered to corresponding models in the navigation system 7 (image space). As a result, objects in physical space are correlated to corresponding models in image space. Therefore, the surgical system 5 always knows the actual position of the surgical tool relative to the patient's anatomy and the planned pose 500, and this information is graphically displayed on the display device 9 during the surgical procedure.

In step S1 of the surgical procedure, a cortical tracking array is attached to the femur 14 to enable the tracking device 8 to track motion of the femur 14. In step S2, the femur 14 is registered (using any known registration technique) to correlate the pose of the femur 14 (physical space) with models of the femur 14 in the navigation system 7 (image space) and the femur checkpoint is attached. In step S3, the femur 14 is prepared to receive a femoral implant (e.g., the femoral component 26) using a navigated femoral broach. In step S4, an acetabular tracking array is attached to the pelvis 12 to enable the tracking device 8 to track motion of the pelvis 12. In step S5, a checkpoint is attached to the pelvis 12 for use during the surgical procedure to verify that the acetabular tracking array has not moved in relation to the pelvis 12. The checkpoint can be, for example, a checkpoint as described in U.S. patent application Ser. No. 11/750,807 (Pub. No. US 2008/0004633), filed May 18, 2007, and hereby incorporated by reference herein in its entirety.

Figure 14C:
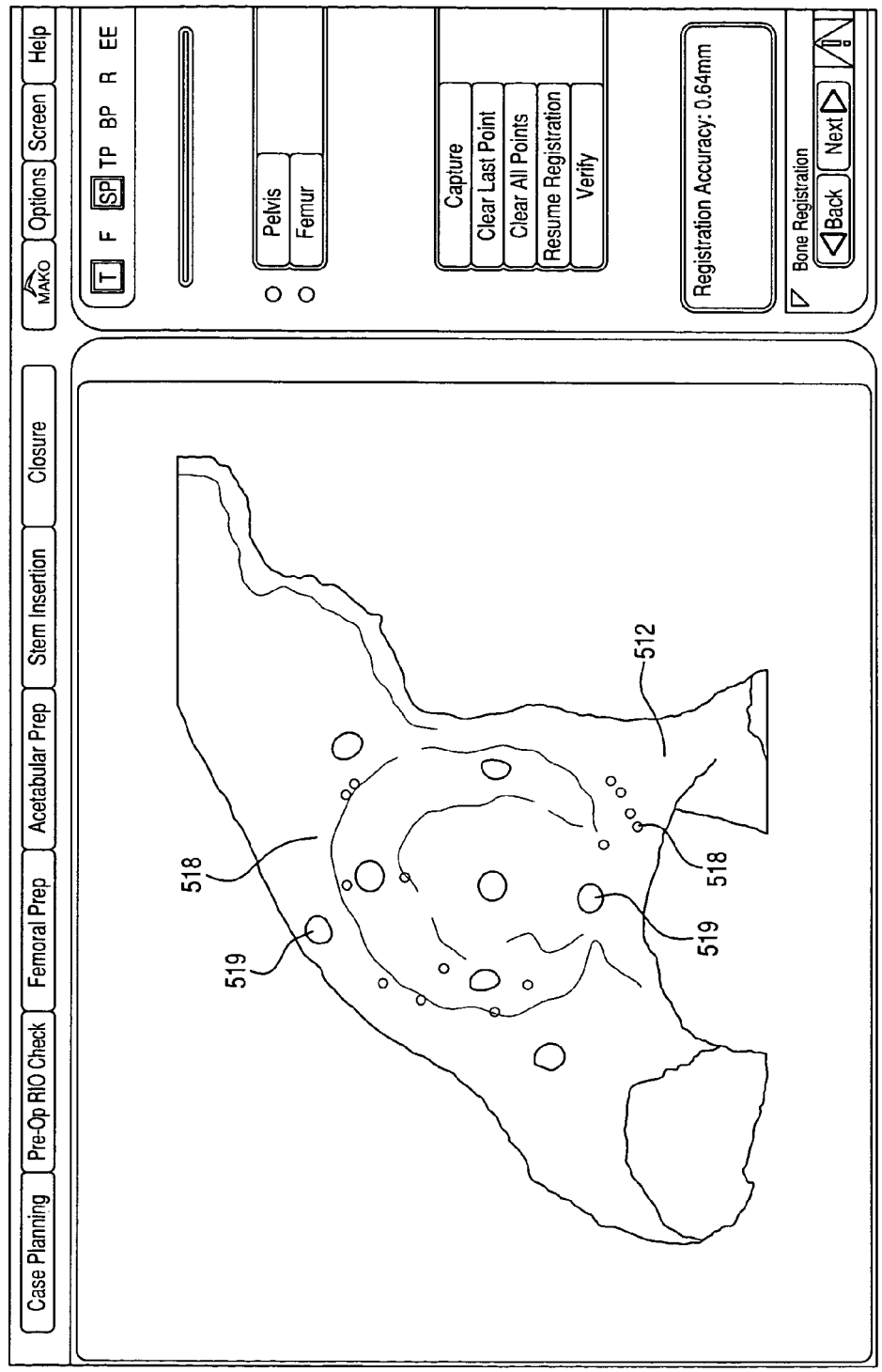

In step S6, the pelvis 12 is registered (using any known registration technique) to correlate the pose of the pelvis 12 (physical space) with model of the pelvis 12 in the navigation system 7 (image space). In one embodiment, as shown in FIG. 14B, registration is accomplished using a tracked probe to collect points on the pelvis 12 (physical space) that are then matched to corresponding points on the representation 512 of the pelvis 12 (image space). In this embodiment, the display device 9 shows the representation 512 of the pelvis 12, including one or more registration points 516. The registration points 516 help the surgeon understand where on the actual anatomy to collect points with the tracked probe. The registration points 516 can be color coded to further aid the surgeon. For example, a registration point 516 on the pelvis 12 to be collected next with the tracked probe can be colored yellow, while registration points 516 that have already been collected can be colored green and registration points 516 that will be subsequently collected can be colored red. After registration, the display device 9 can show the surgeon how well the registration algorithm fit the physically collected points to the representation 512 of the pelvis 12. For example, as shown in FIG. 14C, error points 518 can be displayed to illustrate how much error exists in the registration between the surface of the representation 512 and the corresponding surface of the physical pelvis 12. In one embodiment, the error points 518 can be color coded, for example, with error points 518 representing minimal error displayed in green and error points 518 representing increasing amounts of error displayed in blue, yellow, and red. As an alternative to color coding, error points 518 representing different degrees of error could have different shapes or sizes. Verification points 519 can also be displayed. The verification points 519 illustrate to the surgeon where to collect points with the tracked probe to verify the registration. When a registration point 519 is collected, the software of the navigation system 7 displays the error (e.g., numerically in millimeters) between the actual point collected on the anatomy and the registered location of the representation 512 in physical space. If the registration error is too high, the surgeon re-registers the pelvis 12 by repeating the registration process of step S6.

In step S7, the robotic arm 30 is registered to correlate the pose of the robotic arm 30 (physical space) with the navigation system 7 (image space). The robotic arm 30 can be registered, for example, as described in U.S. patent application Ser. No. 11/357,197 (Pub. No. US 2006/0142657), filed Feb. 21, 2006, and hereby incorporated by reference herein in its entirety.

In step S8, the surgeon resurfaces the acetabulum 22 using a reamer, such as the operating member 100 or the operating member 200, coupled to the robotic arm 30. As described above in connection with the operating members 100, 200, the surgeon couples the appropriate operating member (e.g., a straight or offset reamer) to the end effector 40, connects the cutting element 116 to the received operating member, and manually manipulates the robotic arm 30 (as shown in FIG. 10A) to ream the acetabulum 22. During reaming, the robotic arm 30 provides haptic (force feedback) guidance to the surgeon. The haptic guidance constrains the surgeon's ability to manually move the surgical tool to ensure that the actual bone cuts correspond in shape and location to planned bone cuts (i.e., cuts consistent with the surgical plan).

Figure 12:
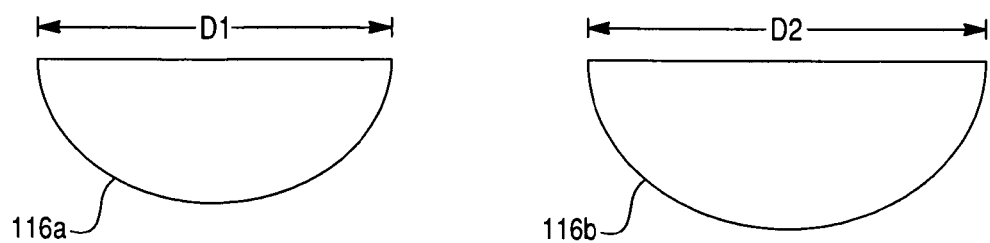
FIG. 12 is a cross-sectional view of an embodiment of a first cutting element and a second cutting element.

Preferably, the constraint is adjusted to correspond to the surgical tool, e.g., the cutting element 116, that is being used. In one embodiment, the controller is programmed to generate force signals that cause the force system to provide a first constraint (e.g., haptic guidance) on the surgeon's manual movement of the end effector 40 when the cutting element 116 is a first cutting element 116a and provide a second constraint (e.g., haptic guidance), different from the first constraint, on the surgeon's manual movement of the end effector 40 when the cutting element 116 is a second cutting element 116b. As shown in FIG. 12, the first and second cutting elements 116a, 116b are hemispherical cutting elements configured to cut the acetabular bone, and a diameter D1 of the first cutting element 116a is different from a diameter D2 of the second cutting element 116b. In one embodiment, the diameter D1 of the first cutting element 116a is less than a diameter D3 of the prosthetic component 316 by a predetermined amount, and the diameter D2 of the second cutting element 116b is greater than the diameter D1 of the first cutting element 116a. In an exemplary embodiment, the predetermined amount is five millimeters less than the diameter D3 of the prosthetic component 316. In other embodiments, the predetermined amount could be greater or less than five millimeters, such as two millimeters, three millimeters, seven millimeters, or a range (e.g., 5±2 millimeters).

Figure 13A:
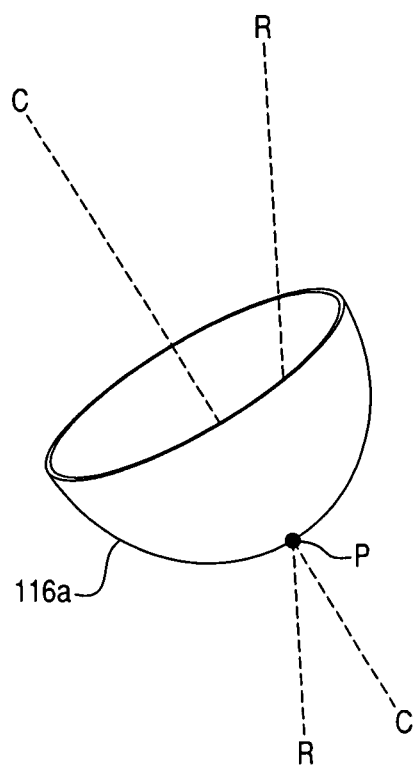
FIG. 13A illustrates an embodiment of a first constraint.

Because the diameter D1 of the first cutting element 116a is smaller than the diameter D3 of the prosthetic component 316, the first cutting element 116a can be used to make preliminary cuts, such as removing articular cartilage and osteophytes. The preliminary cuts do not need to be as accurate as the final cuts. Therefore, the preliminary cuts can be made with a lesser degree of haptic constraint than the final cuts. In particular, when the first cutting element 116a is used for reaming, the first constraint is configured to constrain, along a reference axis R-R, at least one point associated with the cutting element 116a. For example, as shown in FIG. 13A, at least one point P on a central axis C-C of the cutting element 116a can be constrained along the reference axis R-R such that the point P can move only along the reference axis R-R. In the embodiment of FIG. 13A, the point P is disposed on the cutting element 116a. In other embodiments, the point P can be located on the central axis C-C of the cutting element 116a without actually intersecting the cutting element 116a. In this embodiment, the reference axis R-R is a desired axis of the prosthetic component 316 when the prosthetic component 316 is implanted on the anatomy of the patient. For example, the reference axis R-R can be a central axis of the prosthetic component 316 when the prosthetic component 316 is implanted on the acetabulum 22 according to the surgeon's surgical plan. Thus, when reaming with the first cutting element 116a, the robotic arm 30 provides force feedback to constrain the surgeon's manual movement of the end effector 40 so that the point P stays on the reference axis R-R. In this manner, the trajectory of the surgical tool is constrained. In one embodiment, the depth the point P can travel along the reference axis R-R is also constrained to prevent over reaming of the acetabulum 22. Orientation of the end effector 40, however, is preferably unconstrained when the first cutting element 116a is used.

Figure 13B:
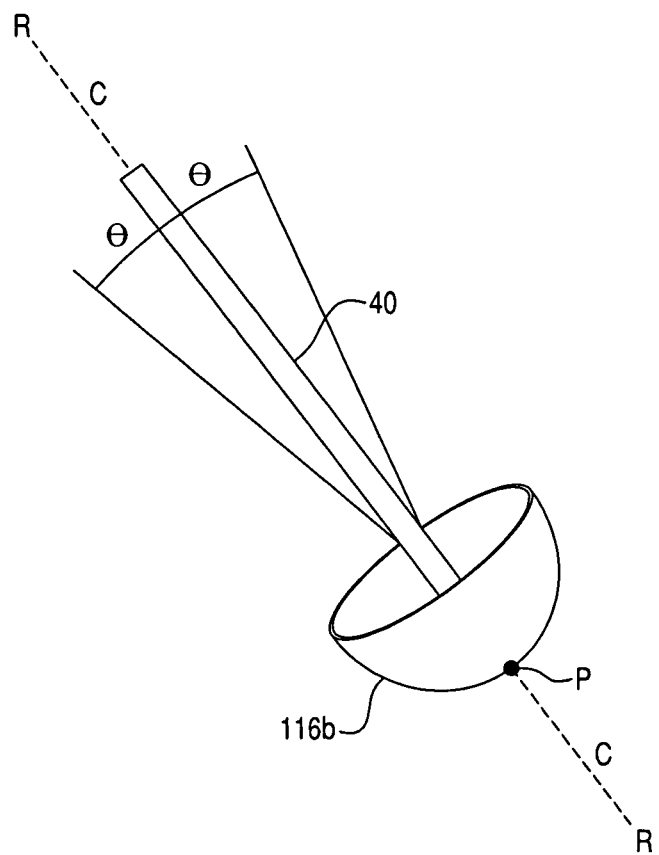
FIG. 13B illustrates an embodiment of a second constraint.

As reaming continues, progressively larger reamers are used. After the preliminary cuts are made, the surgeon replaces the first cutting element 116a with a larger cutting element, such as the second cutting element 116b. When the second cutting element 116b is coupled to the end effector 40, the robotic arm 30 applies the second constraint. The second constraint is configured to constrain an orientation of the surgical tool relative to the reference axis R-R. For example, as shown in FIG. 13B, the robotic arm 30 can apply force feedback to constrain the surgical tool to maintain an axis of the surgical tool within a predefined angular distance θ from the reference axis R-R. The axis of the surgical tool can be, for example, the central axis A-A of the housing 60 of the end effector 40, an axis of a shaft of the surgical tool (e.g., a central axis B-B of the received operating member), or the central axis C-C of the cutting element 116b. The predefined angular distance θ is preferably 10 degrees but could be any other angle suitable for the specific surgical application, such as, for example, 5 degrees, 15 degrees, etc. Preferably, the robotic arm 30 applies both the first and second constraints when the second cutting element 116b is used. Thus, with the second cutting element 116b, the robotic arm constrains both the trajectory and angular orientation of the surgical tool. To avoid over reaming, the depth the surgical tool can travel can also be constrained not to exceed a desired depth of the prosthetic component 316 when implanted on the acetabulum 22. In one embodiment, the second cutting element 116b corresponds in size to the prosthetic component 316 and is used to make the final cut to the acetabulum 22. In one embodiment, the controller is programmed to deactivate or shut off the second cutting element 116b when the shape of the final cut substantially corresponds to a desired shape of the final cut.

Reamers can be sized based on their outside diameter with reamer sizes progressing in 1 millimeter increments. In one embodiment, for all cutting elements that are at least five sizes (e.g., five millimeters) below the size of the planned prosthetic component 316, the robotic arm 30 applies the first constraint. In other words, if the diameter of a cutting element is at least five millimeters less than the diameter D3 of the prosthetic component 316, the cutting element can be used at any angle but is constrained along the reference axis R-R. For larger cutting elements (i.e., four sizes leading up to the size of the planned cup), the robotic arm 30 additionally applies the second constraint so that angular orientation of the surgical tool is also constrained. The angular constraint may become progressively more restrictive as the size of the cutting element increases. In another embodiment, for reamer sizes equal to two sizes below and two sizes above the size of the planned prosthetic component 316, the robotic arm 30 applies both the first and second constraints. Preferably, the depth of travel of the surgical tool is constrained to prevent reaming beyond the planned depth of the prosthetic component 316.

Figure 14D:
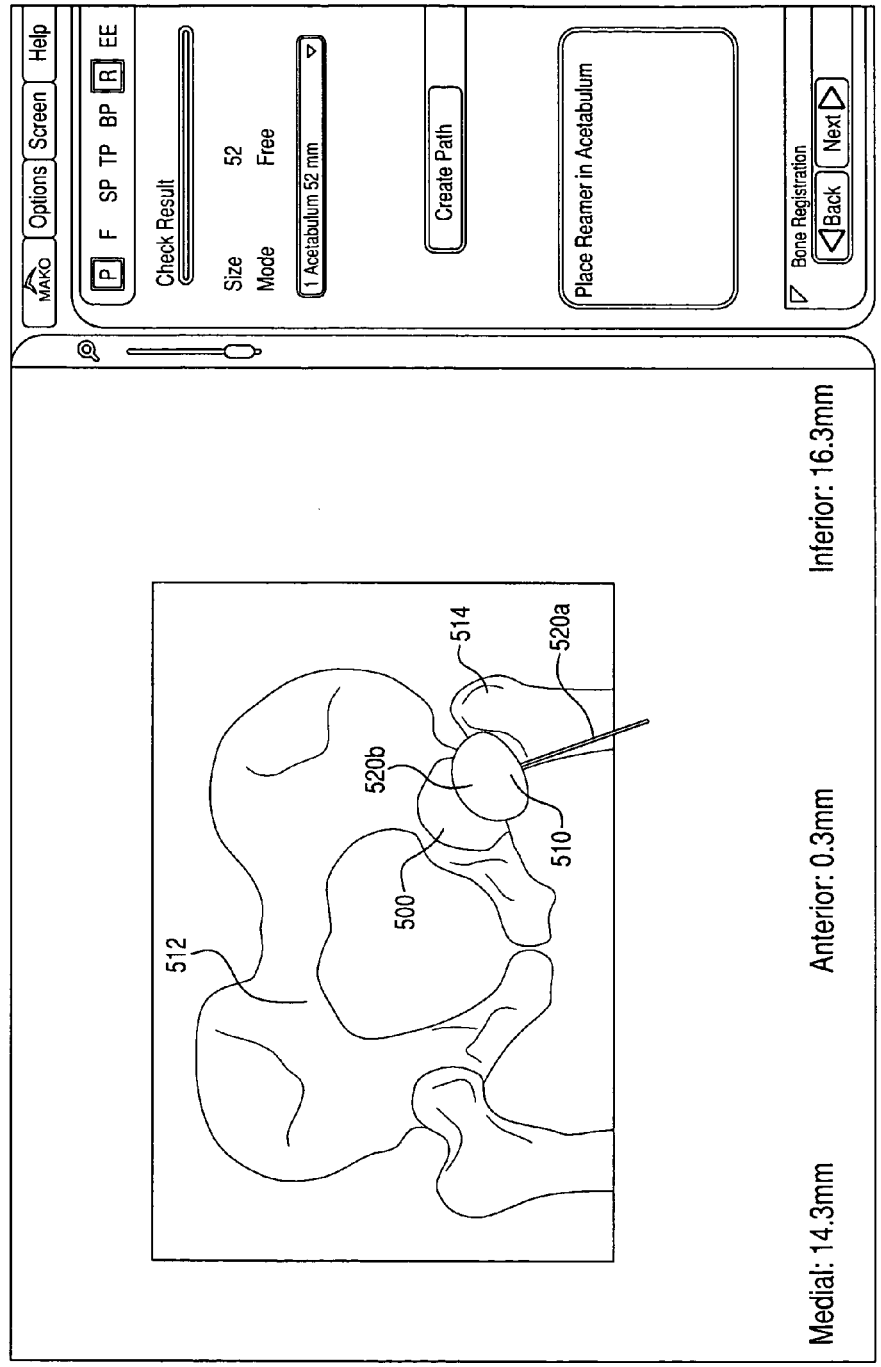

The first and second constraints are preferably activated by the controller that controls the force system of the robotic arm 30. For example, the controller can be programmed to generate control signals that cause the force system to provide at least one of the first constraint and the second constraint when a portion of the cutting element 116 (e.g., the first cutting element 116a or the second cutting element 116b) coincides with an activation region 510. The activation region 510 (shown in FIGS. 14A and 14D) can be a virtual region that is defined relative to the anatomy of the patient. For example, the activation region 510 can be defined relative to the planned pose 500 of the prosthetic component 316. In one embodiment, the activation region 510 coincides with the boundary of the planned pose 500 and therefore has the same shape and location as the planned pose 500. In another embodiment, at least a portion of the planned pose 500 and the activation region 510 coincide. The activation region 510 can also extend beyond a boundary of the planned pose 500. For example, as shown in FIGS. 14A and 14D, the activation region 510 is a cylindrical volume that extends beyond the boundary of the planned pose 500. Preferably, the cylindrical volume is coaxial with an axis of the planned pose 500, such as the central axis C-C of the prosthetic component 316 when the prosthetic component 316 is implanted on the anatomy in the planned pose 500.

Figure 14E:
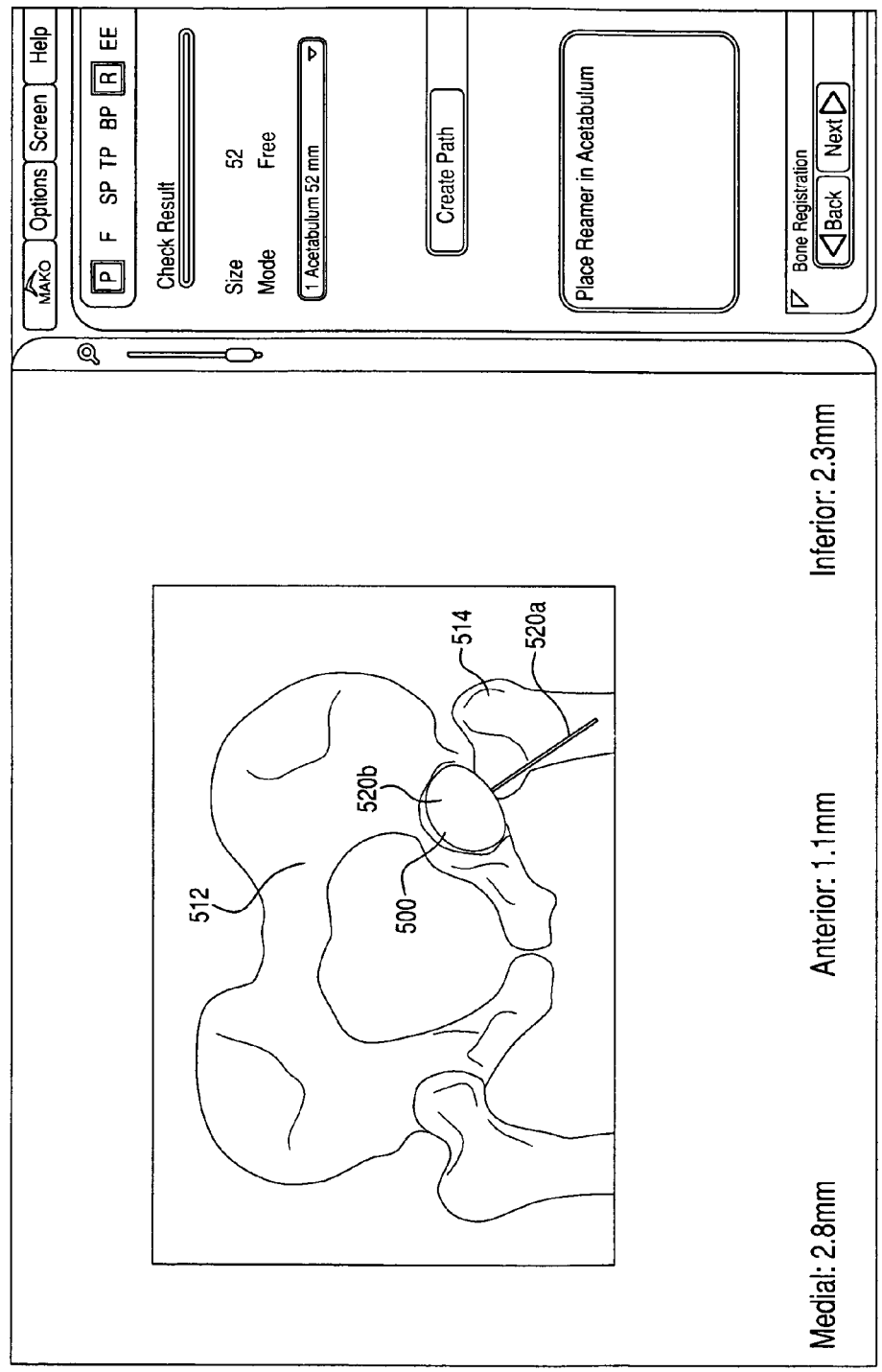

During surgery, a representation of the surgical tool is displayed on the display 9 relative to the planned pose 500, the activation region 510, and/or the representations 512, 514 of the anatomy, as shown in FIG. 14D. The representation is a graphical model in image space that corresponds to the actual surgical tool in physical space (via registration of the robot arm 30 in step S7) and includes a representation 520a of the shaft of the received operating member and a representation 520b of the cutting element 116. The surgeon uses this view to manually navigate the surgical tool into the incision. In one embodiment, the surgeon can freely move the surgical tool until a portion of the surgical tool intersects the activation region 510 at which time the force system controls the robotic arm 30 to provide the appropriate constraint (e.g., the first constraint and/or the second constraint). In one embodiment, the appropriate constraint activates when the representation 520a of the shaft of the received operating member is completely bounded by the cylindrical volume of the activation region 510, as shown in FIG. 14D. Once the appropriate constraints are active, the activation region 510 can be removed from the displayed image, as shown in FIG. 14E.

The first and second constraints ensure that the bone cuts to the acetabulum accurately correspond to the bone cuts of the planned pose 500 of the prosthetic component 316. Because the first and second constraints are applied by actuators, the first and second constraints are not infinite. Accordingly, the surgeon may be able to override the first and second constraints by manually moving the end effector 40 with sufficient force to overcome the force feedback provided by the robotic arm 30. To avoid damage to the patient and/or inaccurate bone cuts, the controller is preferably programmed to automatically control at least one aspect of the pose of the surgical tool if the surgeon manually overrides the first constraint and/or the second constraint. For example, during reaming, if the surgeon pushes the end effector 40 such that the shaft of the received operating member exceeds the predefined angular distance θ from the reference axis R-R, the robotic arm 30 can apply active force feedback to try to move the shaft of the received operating member back within the predefined angular distance θ. Another option is for the controller to deactivate or shut off the reamer if the first constraint and/or the second constraint is overridden by the surgeon.

In step S9, the surgeon verifies that the registration (i.e., the geometric relationship) between the acetabular tracking array and the pelvis 12 is still valid by contacting the pelvis checkpoint with a tracked probe as described, for example, in U.S. patent application Ser. No. 11/750,807 (Pub. No. US 2008/0004633), filed May 18, 2007, and hereby incorporated by reference herein in its entirety. If registration has degraded (e.g., because the acetabular tracking array was bumped during reaming), the pelvis 12 is re-registered. Registration verification can be performed any time the surgeon wants to check the integrity of the acetabular registration.

In step S10, the prosthetic component 316 is implanted on the reamed acetabulum 22 using an impactor tool, such as the operating member 300 or the operating member 400, coupled to the robotic arm 30. As described above in connection with the operating members 300, 400, the surgeon removes the reamer from the end effector 40, connects the appropriate operating member (e.g., a straight or offset impactor) to the end effector 40, and attaches the prosthetic component 316 (e.g., the acetabular cup 28a) to the operating member. The surgeon then manually manipulates the robotic arm 30 (as shown in FIG. 10B) to impact the prosthetic component 316 on the acetabulum 22. While the surgeon impacts the prosthetic component 316, the robotic arm 30 provides haptic guidance, based on the surgical plan, that constrains the surgeon's ability to move the surgical tool to ensure that the actual pose of the prosthetic component 316 that is coupled to the surgical tool substantially corresponds to the planned pose 500 when the prosthetic component 316 is impacted onto the acetabulum 22. In one embodiment, the controller is programmed to compare a target pose (e.g., the planned pose 500 and/or the activation region 510) of the prosthetic component 316 and an actual pose of the prosthetic component 316 engaged by the surgical tool and to generate control signals that cause the force system to allow movement of the surgical tool within a range of movement and provide haptic feedback to constrain the surgeon's ability to manually move the surgical tool beyond the range of movement. The range of movement can be defined, for example, relative to a desired aspect of the prosthetic component 316 when the prosthetic component 316 is implanted on the anatomy, such as an angle (e.g., a version angle, an inclination angle), an axis, an orientation, a center of rotation, a boundary, and/or a depth. The haptic feedback can then resist movement of the surgical tool by the surgeon that would cause substantial deviation between at least one aspect of the actual pose of the prosthetic component 316 and a corresponding desired aspect of the target pose of the prosthetic component 316. The haptic feedback can be applied as the surgeon is moving the prosthetic component 316 toward the implantation site and is preferably maintained as the surgeon implants the prosthetic component 316 on the anatomy. As a result, the acetabular cup 28a can be implanted on the acetabulum 22 such that the inclination accuracy, version accuracy, and center of rotation of the acetabular cup 28a substantially correspond to the surgical plan.

In a manner identical to that described above in connection with step S8 (reaming), during the impaction step S10, the display device 9 can show the planned pose 500, the activation region 510, the representations 512, 514 of the anatomy, and a representation of the surgical tool. During impaction, however, the representation 520b represents the prosthetic component 316 as opposed to the cutting element 116. Additionally, as described above in connection with step S8, the controller can activate the haptic feedback during the impaction procedure when at least a portion of the actual pose of the surgical tool coincides with at least a portion of the activation region 510 of the target pose. Also as described above in connection with step S8, if the surgeon moves the end effector 40 to override the haptic feedback, the controller can initiate automatic control of the surgical tool to substantially align at least one aspect of the actual pose with the corresponding desired aspect of the target pose.

Figure 14F:
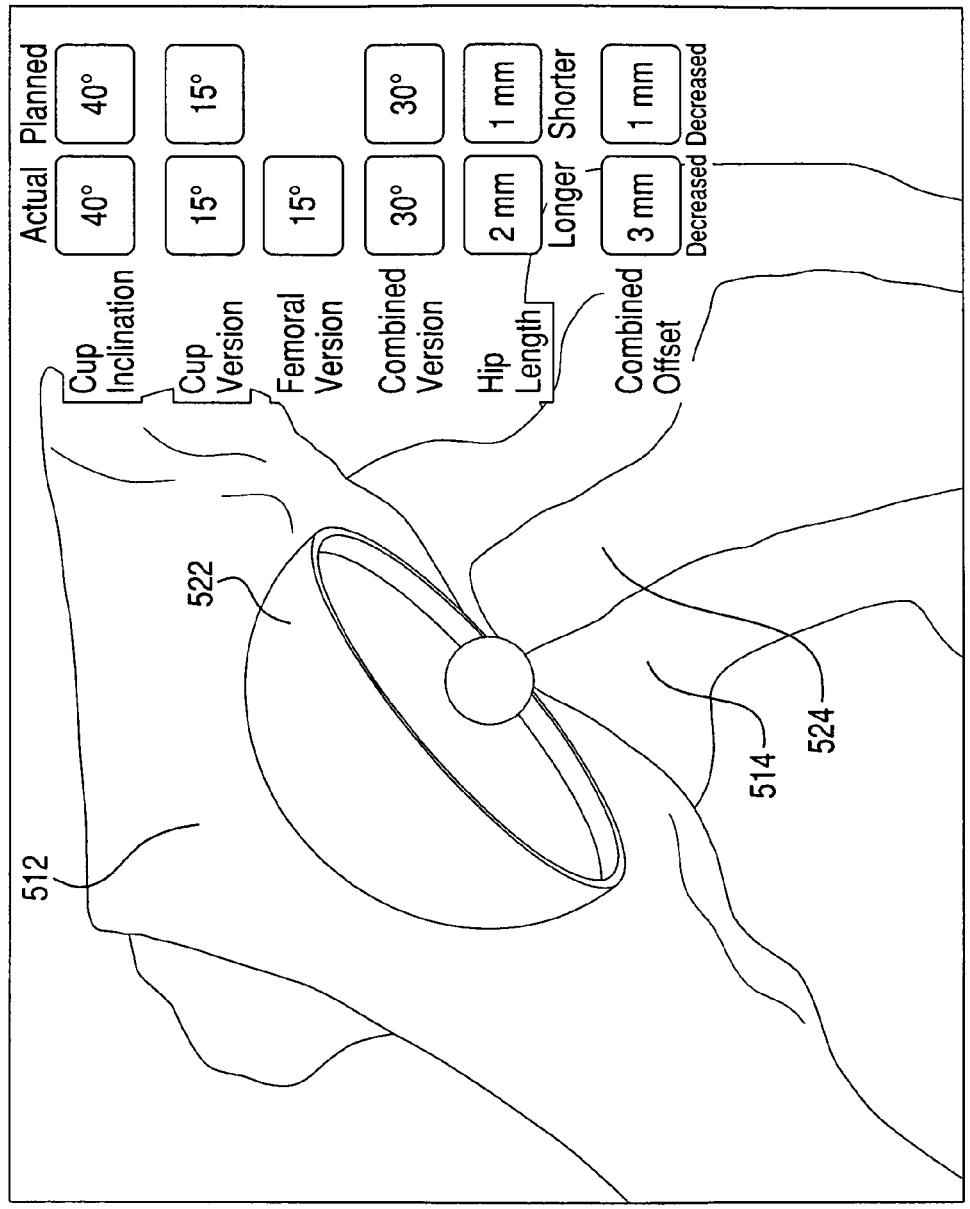
Figure 14G:
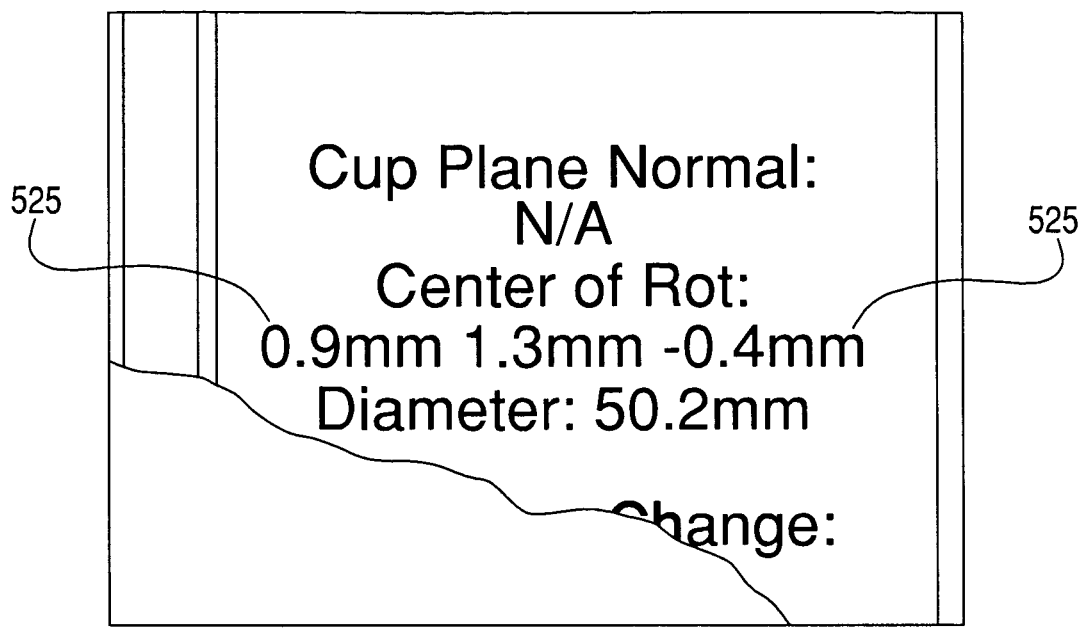

In step S11, the surgeon installs the femoral component 26 on the femur 14, and in step S12, the surgeon determines leg length and femoral offset. As shown in FIG. 14F, the display device 9 can display a representation 522 of the implanted acetabular component 28 and a representation 524 of the implanted femoral component 26. Additionally, as shown in FIG. 14G, at any time during the surgical procedure, the display device 9 can show data related to progress and/or outcome. For example, after reaming in step S8 and/or impacting in step S10), data 525 relating to the actual position of the reamed acetabulum 22 (or the implanted acetabular cup 28a) can include, for example, numerical data representing error between the actual and planned locations in the three orthogonal planes of the patient's anatomy (i.e., medial/lateral, superior/inferior, and anterior/posterior).

Parking Configuration

The surgical system 5 preferably is configured to park or hold the robotic arm 30, for example, during a surgical procedure when the surgeon is not actively using the robotic arm 30 to perform a task. The parking configuration applies to a moveable member of the robotic arm 30, such as the articulated arm 34 or an instrumented linkage that is used to track an object (e.g., a mechanical tracking arm) as described, for example, in U.S. Pat. No. 6,322,567, which is hereby incorporated by reference herein in its entirety. In the parking configuration, the moveable member is secured in a safe position, and the working end of the moveable member (e.g., the surgical tool) is prevented from drifting outside the sterile field of the surgical procedure.

The surgical system 5 preferably is configured to account for different weights of objects connected to the robotic arm 30. As explained above, the robotic arm 30 is configured to permit a user (e.g., the surgeon) to manually move the articulated arm 34 to permit an object coupled to the articulated arm 34 (e.g., the received operating member) to be manipulated in space and thereby facilitate the performance of a task (e.g., bone cutting, implant impaction) using the coupled object. The articulated arm 34 is adapted to couple to multiple interchangeable objects, such as a first object and a second object. The first object could be, for example, the operating member 100 or the operating member 200, and the second object could be the operating member 300 or the operating member 400 (or vice versa). Because the operating members 100, 200, 300, 400 have different configurations and functions, they may also have substantially different weights. For example, in one embodiment, a weight of the second object is at least three times greater than a weight of the first object. In another embodiment, a weight of the second object is at least thirty-six percent greater than a weight of the first object. In another embodiment, a weight of the second object is at least fifty-two percent greater than a weight of the first object. In another embodiment, a weight of the second object is at least ninety-four percent greater than a weight of the first object. In another embodiment, a weight of the operating member 100 is about 360 grams, a weight of the operating member 200 is about 460 grams, a weight of the operating member 300 is about 490 grams, and a weight of the operating member 400 is about 700 grams. Thus, the parking configuration is configured to accommodate payloads of the robotic arm 30 that have substantially different weights.

The parking configuration can be achieved using a brake. In operation, the brake limits manual movement of at least a portion of the moveable member. For example, the brake limits manual movement of at least a portion of the articulated arm 34 to inhibit manipulation in space of the coupled object. Because the articulated arm 34 is used with multiple operating members during a single surgical procedure, the brake should work both when the articulated arm 34 is coupled to the first object and when the articulated arm 34 is coupled to the second object without requiring mechanical reconfiguration of the brake, which would disrupt surgical workflow. The brake can be implemented using any suitable combination of mechanical and/or electrical components. In one embodiment, the brake is a virtual brake. In contrast to a physical brake, the virtual brake does not include conventional mechanical brake components. Instead, as explained below, the virtual brake is implemented using the controller and the force system of the robotic arm 30.

Figure 15:
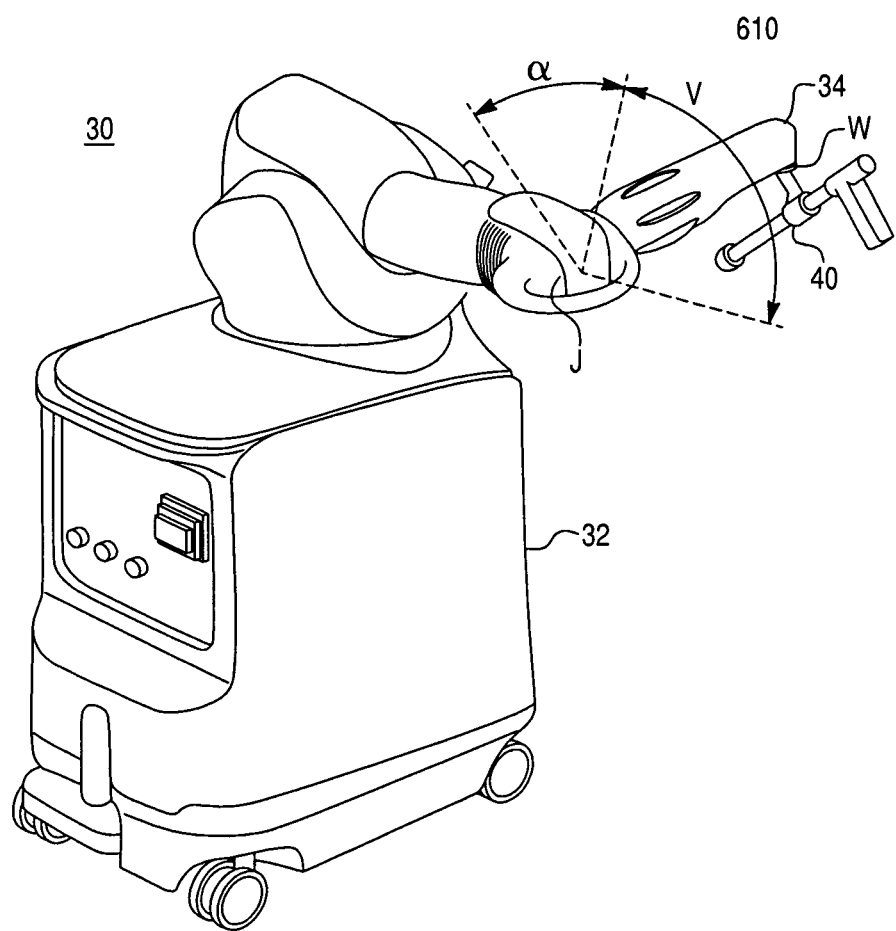
FIG. 15 illustrates an embodiment of a virtual brake.

In one embodiment, the virtual brake is implemented by controlling one or more actuators of the force system to apply a holding torque (i.e., a braking force) to one or more joints of the articulated arm. Application of the holding torque is based on a position of the articulated arm 34 relative to a braking region where the brake is configured to engage when the surgeon moves at least a portion of the articulated arm 34 (such as one or more joints) into the braking region. In particular, the brake is configured to apply the braking force only if the joint (or joints) is in the braking region. For example, the brake can be configured to limit manual movement of the joint (or joints) based on the braking region, which can be defined, for example, by a position of the joint (or joints). In one embodiment, the braking region is a defined angular range of motion α of a joint J of the articulated arm 34 and can also include angular ranges of motion of other joints of the articulated arm 34. The angular range of motion α can be any range of motion that places the articulated arm 34 in a desired parking configuration. For example, FIG. 15 shows the joint J in a substantially horizontal position. In this embodiment, to park the joint J in a substantially vertical position, the joint J is moved from the horizontal position to the vertical position. In one embodiment, the angular range of motion α of the substantially vertical position is about +/−15 degrees. In other embodiments, the angular range of motion α can be, for example, about +/−15 degrees, about +/−30 degrees, or about 180+/−30 degrees. In one embodiment, the most distal joint can have an angular range of motion α of about +/−30 degrees or about 180+/−30 degrees. The brake is configured to engage (and hold the joint J in the braking region) when the surgeon moves the joint J into the braking region. For example, the surgeon moves the joint J from the horizontal position approximately 90 degrees in a direction V until the position of the joint J is within the angular range of motion α. When the position of the joint J is within the angular range of motion α, the controller generates a signal that controls the actuator of the joint J to apply the holding torque. When the holding torque is applied, the brake is engaged and the joint J stays locked in position. When the joint J moves into this braking region, the controller preferably also generates signals that control the actuators of one or more other joints of the articulated arm 34 to apply holding torque resulting in a plurality of braked joints. As a result, the overall position of the articulated arm 34 is locked in the parking configuration. The surgeon can then safely leave the articulated arm 34 unattended, change the operating member, or perform any other task without worrying that the surgical tool will drift outside the sterile field or interfere with the patient or other equipment in the operating room. Although the above description results in engagement of the brake when the joint J is within the angular range of motion α, the brake can also be configured to engage only if multiple joints are moved within their respective angular ranges of motion.

Disengagement of the brake can also be based on the braking region. In one embodiment, the brake is configured to disengage when the surgeon moves at least one of the braked joints (such as the joint J) outside the braking region of that particular joint. For example, to disengage the brake, the surgeon moves the articulated arm 34 with sufficient force to overcome the applied holding torque or braking force of the joint J. The magnitude of the braking force is small enough to enable the surgeon to manually move the articulated arm 34 to overcome the braking force. The braking force can be adjusted for a particular surgeon and/or a particular surgical procedure, and different joints can have different braking forces. For example, the braking force can be in a range of about 5 to 12 Nm. For example, in one embodiment, the first joint (i.e., the most proximal joint) can have a braking force of about 6 Nm, the second joint can have a braking force of about 12 Nm, the third joint can have a braking force of about 9 Nm, the fourth joint can have a braking force of about 11 Nm, the fifth joint can have a braking force of about 7 Nm, and the sixth joint (i.e., the most distal joint) can have a braking force of about 5 Nm. When the joint J moves outside the braking region into an unbraked region 610, the controller generates a signal that controls the actuator of the joint J (and any other braked joints) to discontinue application of the holding torque. The surgeon can then freely move the articulated arm 34. In one embodiment, an overlap exists between the braking region and the unbraked region 610 to prevent accidental release of the brake. Additionally or alternatively, the brake can be configured to disengage independent of the braking region. For example, if the articulated arm 34 includes one or more braked joints and at least one unbraked joint, such as a wrist joint W, the brake can be configured to disengage when the surgeon manually moves the unbraked joint, for example, by twisting the wrist joint W. Although the above description results in disengagement of the brake when the joint J is moved outside the angular range of motion α, the brake can also be configured to disengage only if multiple joints are moved outside their respective angular ranges of motion.

One advantage of the holding torque embodiment is that the brake is implemented in joint space, and each individual joint actuator can have a unique holding torque limit. For example, a heavier joint may require a larger holding torque because, in addition to braking, the holding torque also has to compensate for gravitational forces acting on the joint. In contrast, a light weight joint can have a relatively small holding torque because the lighter joint requires less gravity compensation. This distinction can be used to facilitate disengagement of the brake. In particular, because it is easier for the surgeon to manually move a joint that has a lower holding torque, movement of lighter joints can be used to trigger disengagement of the virtual brake.

Figure 16A:
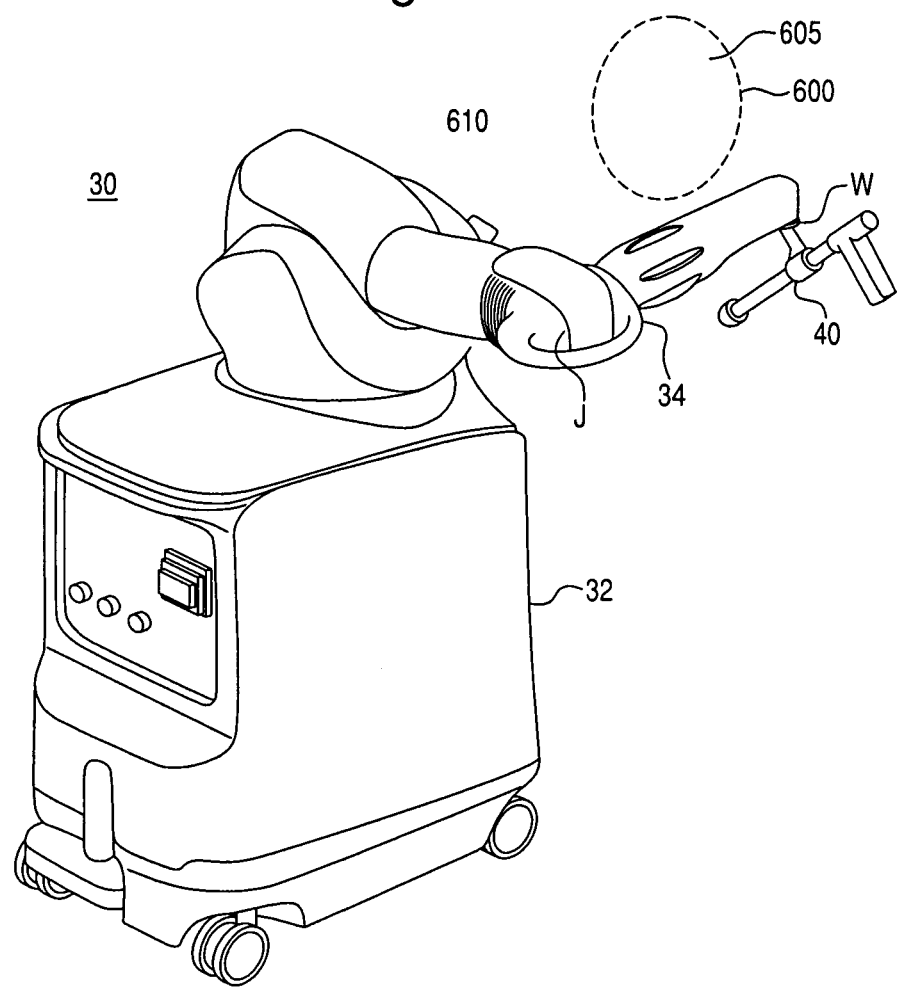
FIG. 16A illustrates an embodiment of a virtual brake that is disengaged.
Figure 16B:
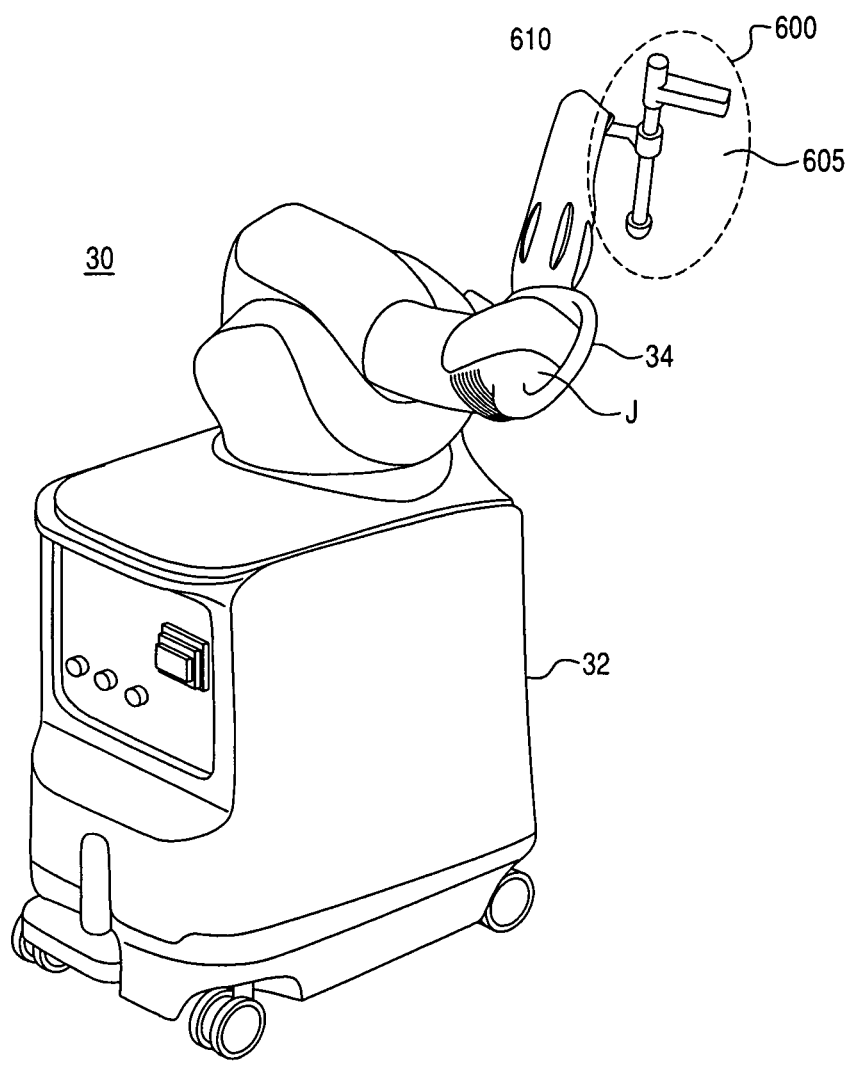
FIG. 16B illustrates an embodiment of a virtual brake that is engaged.

In another embodiment, the virtual brake is implemented in Cartesian space using a haptic object. The haptic object embodiment is similar to the holding torque embodiment except the braking region is defined by a haptic object instead of an angular range of motion of a joint. As explained in U.S. patent application Ser. No. 11/357,197 (Pub. No. US 2006/0142657), filed Feb. 21, 2006, which is hereby incorporated by reference herein in its entirety, a haptic object is a virtual object defined by a mapping between force and/or torque (i.e., force feedback) and position. The haptic object is registered to physical space and defines a virtual boundary in physical space. The haptic object can be defined so that the virtual boundary has any desired size, shape, and location appropriate for a particular surgical procedure. In a manner similar to a virtual cutting boundary activated during bone cutting, movement of a specified portion of the articulated arm 34 beyond the virtual boundary is constrained by force feedback applied by the force system. When a haptic object is used as a virtual brake, the haptic object functions as "virtual holster" for the surgical tool or other equipment attached to the end of the articulated arm 34, and the force feedback applied by the force system is the braking force. As shown in FIGS. 16A and 16B, the virtual holster includes a virtual boundary 600 (a first region) and an interior region 605 (a second region) that is bounded by the virtual boundary 600. When the surgeon manually moves the surgical tool inside the virtual boundary 600, the controller controls the force system to constrain motion of the articulated arm 34 such that the surgical tool is maintained within the virtual boundary 600 of the virtual holster.

In the holding torque embodiment, the braking force is substantially continuous in the braking region because a constant holding torque is applied regardless of the position of the joint J within the braking region. As a result, the articulated arm 34 has a smooth continuous feel as the surgeon moves the joint J in the braking region. In contrast, in the haptic object embodiment, the braking force is substantially discontinuous in the braking region because the braking force is typically applied at the virtual boundary 600 of the haptic object but not within the interior region 605 of the haptic object. For example, in one embodiment, force feedback is applied only at or near the virtual boundary 600 but not in the interior region 605. Thus, when the surgical tool is parked in the virtual boundary 600, the surgical tool can drift freely within the confines of the virtual boundary 600 but is prevented from drifting outside the virtual boundary 600. In this manner, the braking region includes a first region (i.e., the virtual boundary 600) in which a braking force is applied and a second region (i.e., the interior region 605) in which the braking force is not applied. Alternatively, the mapping of the haptic object can be defined such that force feedback is applied in the interior region 605 as well as at or near the virtual boundary 600 so that the surgical tool does not drift within or beyond the virtual boundary 600.

As described above in connection with the holding torque embodiment, in the haptic object embodiment, the brake is configured to engage when the surgeon manually moves the surgical tool (or other specified portion of the articulated arm 34) into the braking region. For example, when the surgeon moves the articulated arm 34 from the location shown in FIG. 16A to the location shown in FIG. 16B, the surgical system 5 detects when a specified portion of the surgical tool (such as the tip and/or shaft) is within the virtual boundary 600, and the controller engages the brake. In the haptic object embodiment, engaging the brake can include an affirmative action, such as turning on the force feedback of the haptic object when the surgical tool is within the virtual boundary 600. Alternatively, the force feedback of the haptic object can be continuously active so that engaging the brake includes the surgical system 5 determining that the surgical tool is within the virtual boundary 600. In this manner, the controller is programmed to determine whether at least a portion of the articulated arm 34 is in a defined braking region and generate a signal configured to cause a defined braking force to be applied to inhibit movement of at least the portion of the articulated arm 34 when at least the portion of the articulated arm 34 is determined to be in the braking region. Disengagement of the brake can also be based on the braking region. In one embodiment, the brake is configured to disengage when the surgeon moves the surgical tool (or other specified portion of the articulated arm 34) outside the braking region. For example, to disengage the brake, the surgeon moves the articulated arm 34 with sufficient force to overcome the force feedback applied by the force system at the virtual boundary 600. When the surgical tool moves outside the virtual boundary 600 into the unbraked region 610, the brake is disengaged. In the haptic object embodiment, disengaging the brake can include an affirmative action, such as turning off the force feedback of the haptic object after the surgical tool has moved outside the virtual boundary 600. Alternatively, the force feedback of the haptic object can be continuously active so that disengaging the brake includes the determination by the surgical system 5 that the surgical tool is outside the virtual boundary 600. As with the holding torque embodiment, the magnitude of the braking force is small enough to enable the surgeon to manually move the articulated arm 34 to overcome the braking force. In one embodiment, an overlap exists between the braking region and the unbraked region 610 to prevent accidental release of the brake. Additionally or alternatively, the brake can be configured to disengage independent of the braking region, such as by twisting the wrist joint W as explained above in connection with the holding torque embodiment.

Figure 17A:
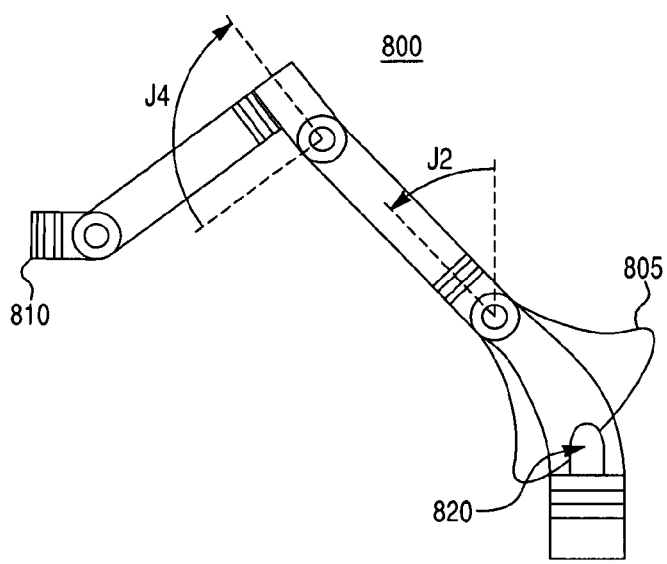
FIG. 17A illustrates an embodiment of an instrumented linkage.

The parking configuration can be used with any moveable member of the robotic arm 30 or with a moveable member that is not associated with the robotic arm 30. For example, the moveable member can be an instrumented linkage system for surgical navigation. In one embodiment, as shown in FIG. 17A, the instrumented linkage system includes an instrumented linkage (or articulated member) 800 having a plurality of links connected by a plurality of moveable joints. As is well known, the joints are instrumented (e.g., using joint encoders) to enable measurement of the coordinates of a proximal link 805 relative to a distal link 810. When the distal link 810 is connected to an object to be tracked (such as a bone), the pose of the tracked object can be determined. As the tracked object moves, the instrumented linkage 800 moves along with the tracked object. In this manner, the pose of the tracked object can be tracked as the tracked object moves in physical space. One advantage of using an instrumented linkage system for tracking is that the instrumented linkage system enables surgical navigation without having a line-of-sight constraint. In contrast, an optical tracking system requires a line of sight between an optical camera and trackable markers disposed on the tracked object.

Figure 17B:
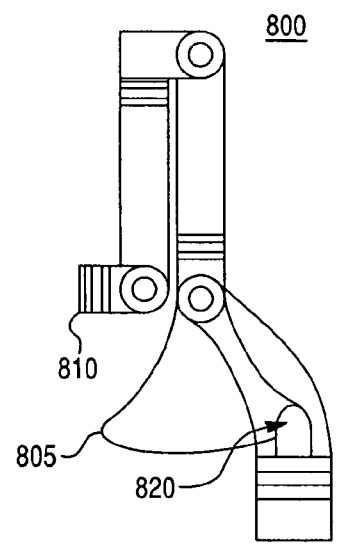
FIG. 17B illustrates an embodiment of the instrumented linkage of FIG. 17A in a parking configuration.

During a surgical procedure, the instrumented linkage 800 can be configured to be disposed in a parking configuration where the instrumented linkage 800 is secured in a safe position and is prevented from drifting outside the sterile field of the surgical procedure. As described above in connection with the articulated arm 34, the parking configuration for the instrumented linkage 800 can be achieved using a brake. The brake can be implemented using a virtual brake (e.g., as described above) or a physical brake. In one embodiment, a joint J2 is coupled with an actuator either directly or through cabling such that the instrumented linkage 800 is back-drivable. During normal operation, the actuator can apply a torque to compensate for a gravity load due to the weight of the instrumented linkage 800. The parking configuration (shown in FIG. 17B) can be achieved by applying a holding torque to at least one joint of the instrumented linkage 800. In one embodiment, the parking configuration can be implemented with a physical brake mechanism 820 using any suitable combination of electro or/and mechanical brakes, electrorheological (ER) or magnetorheological (MR) fluid brakes, and/or the like. As described above in connection with the articulated arm 34, application of the brake is preferably based on a position of the instrumented linkage 800 relative to a braking region. In a preferred embodiment, the brake mechanism 820 is configured to apply a braking force only if a joint (or joints) of the instrumented linkage 800 is in the braking region. For example, the brake can be configured to engage (based on a signal from the controller) when the joint J2 and a joint J4 are each within a pre-defined angular range of motion, for example, as described above in connection with the articulated arm 34. The angular range of motion can be, for example, 10 degrees. Disengagement of the brake can be also based on the breaking region. In one preferred embodiment, the brake is configured to disengage when the surgeon moves at least one of the joints outside of the braking region. For example, the brake can be configured to disengage when the surgeon moves the joint J4 outside the range of motion of the braking region. In this manner, a surgical system can include an articulated member configured to be connected to an object to be tracked and a controller programmed to determine whether at least a portion of the articulated member is in a defined braking region and generate a signal configured to cause a braking force to be applied to inhibit movement of at least the portion of the articulated member when at least the portion of the articulated member is determined to be in the braking region.

Preferably parameters of the virtual brake can be adjusted depending on circumstances and/or desired configurations. According to an embodiment, the virtual brake is defined by a virtual brake configuration that includes parameters such as the braking force, a size of the braking region, a location of the braking region, and/or a shape of the braking region. As explained above in connection with the holding torque and haptic object embodiments, these parameters of the can be tailored for a particular surgical application. Additionally, the controller can be programmed to enable the surgeon to continuously control the virtual brake configuration. For example, before, during, and/or after a surgical procedure, the surgeon can use a computer (such as a computer on the navigation system 7) to adjust one or more of the parameters of the virtual brake configuration. In this manner, the controller is programmed to enable the surgeon to continuously modify the parameters of the virtual brake configuration. Advantageously, the virtual brake configuration can be modified without changing a mechanical configuration of the robotic arm 30. For example, the actuators of the force system are capable of applying varying levels of holding torque and force feedback. Thus, to modify the braking force, the controller simply needs to control the actuators to output a different magnitude of holding torque or force feedback. Similarly, to modify the braking region, the controller simply needs to be provided with new values for the angular range of motion α, the size of the virtual boundary 600, the location of the virtual boundary 600, and/or the shape of the virtual boundary 600. Thus, the virtual brake configuration can be modified at any time. For example, if an operating member that is extremely heavy is going to be coupled to the articulated arm 34, the surgeon may want to increase the braking force to ensure the brake can safely hold the heavy operating member. Similarly, for operating members having different functions, the surgeon may prefer braking regions in different locations. Although the virtual brake configuration can be modified at any time, for a particular surgical procedure, to enable continuous surgical workflow, it is preferable to have a brake that has the same configuration regardless of what object is coupled to the articulated arm 34. This can be accomplished by setting the parameters of the virtual brake configuration to ensure that the brake can safely accommodate all objects that will be coupled to the articulated arm 34 during the surgical procedure.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A tool, comprising:
   an operating member;
   a housing including a receiving portion configured to receive at least a portion of the operating member so as to permit rotation of the operating member relative to the housing while constraining movement of the operating member in a radial direction of the operating member; and
   a coupling device disposed on the housing and configured to couple the operating member to the housing so as to permit rotation of the operating member relative to the housing,
   wherein the coupling device includes a retaining member configured to engage the operating member to constrain movement of the operating member relative to the housing in a longitudinal direction of the operating member, wherein the retaining member is configured to rotate relative to the housing,
   wherein the tool comprises an end effector and further comprises a robotic arm, and wherein the end effector is configured to be mounted to an end of the robotic arm.

2. The tool of claim 1, wherein the retaining member is configured to rotate relative to the operating member.

3. The tool of claim 1, wherein the retaining member is configured to be moveable between first and second positions and is configured to constrain the operating member when the retaining member is in the first position and permit decoupling of the operating member from the housing when the retaining member is in the second position.

4. The tool of claim 3, further comprising a release member coupled to the coupling device and configured to move the retaining member between the first position and the second position.

5. The tool of claim 1, wherein the retaining member includes a first portion configured to move along the longitudinal direction and a second portion configured to move along the radial direction in response to movement of the first portion along the longitudinal direction.

6. The tool of claim 5, wherein the second portion is configured to move along the radial direction to engage a portion of the operating member.

7. The tool of claim 6, wherein the receiving portion has at least one hole therein, and the first portion is disposed outward relative to the receiving portion and the second portion moves inward in the hole along the radial direction to engage the operating member.

8. The tool of claim 5, wherein the first portion includes a surface configured to engage the second portion and displace the second portion in the radial direction as the first portion moves from the first position to the second position.

9. The tool of claim 8, wherein the surface includes a race and the second portion includes a ball bearing.

10. The tool of claim 5, wherein the first portion and the second portion are configured to rotate relative to one another.

11. The tool of claim 1, further comprising a stop member configured to engage the operating member to limit movement of the operating member relative to the housing.

12. The tool of claim 11, wherein the stop member is disposed remotely from the coupling device.

13. The tool of claim 1, wherein the robotic arm is configured to constrain the angular orientation of the operating member.

14. The tool of claim 1, wherein the operating member is a surgical cutting instrument.

15. The tool of claim 14, wherein the operating member is a reamer.

* * * * *